US010686205B2

(12) United States Patent
Reguera et al.

(10) Patent No.: US 10,686,205 B2
(45) Date of Patent: *Jun. 16, 2020

(54) BIOFUEL AND ELECTRICITY PRODUCING FUEL CELLS AND SYSTEMS AND METHODS RELATED TO SAME

(71) Applicant: Board of Trustees of Michigan State University, East Lansing, MI (US)

(72) Inventors: Gemma Reguera, Lansing, MI (US); Allison Speers, East Liverpool, OH (US); Jenna Young, Athens, GA (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 207 days.

This patent is subject to a terminal disclaimer.

(21) Appl. No.: 15/589,950

(22) Filed: May 8, 2017

(65) Prior Publication Data

US 2017/0271702 A1    Sep. 21, 2017

Related U.S. Application Data

(62) Division of application No. 13/635,137, filed as application No. PCT/US2011/028807 on Mar. 17, 2011, now Pat. No. 9,716,287.

(60) Provisional application No. 61/314,936, filed on Mar. 17, 2010.

(51) Int. Cl.
| H01M 8/16 | (2006.01) |
| C12P 7/06 | (2006.01) |
| C12P 7/08 | (2006.01) |
| C12P 7/10 | (2006.01) |
| C12P 39/00 | (2006.01) |
| C12P 7/14 | (2006.01) |
| H01M 8/22 | (2006.01) |

(52) U.S. Cl.
CPC .......... H01M 8/16 (2013.01); C12P 7/065 (2013.01); C12P 7/08 (2013.01); C12P 7/10 (2013.01); C12P 7/14 (2013.01); C12P 39/00 (2013.01); H01M 8/22 (2013.01); *H01M 2250/00* (2013.01); *Y02E 50/13* (2013.01); *Y02E 50/16* (2013.01); *Y02E 50/17* (2013.01); *Y02E 50/343* (2013.01); *Y02E 60/527* (2013.01)

(58) Field of Classification Search
CPC ...... H01M 8/16; H01M 2250/00; H01M 8/22; C12P 7/14; C12P 7/08; C12P 7/065; C12P 7/10; C12P 39/00; Y02E 50/17; Y02E 50/343; Y02E 60/527; Y02E 50/16; Y02E 50/13

See application file for complete search history.

(56) References Cited

U.S. PATENT DOCUMENTS

| 4,600,590 A | 7/1986 | Dale |
| 5,037,663 A | 8/1991 | Dale |
| 6,106,888 A | 8/2000 | Dale et al. |
| 7,176,176 B2 | 2/2007 | Pickenhagen et al. |
| 9,716,287 B2 | 7/2017 | Reguera et al. |
| 10,074,867 B2* | 9/2018 | Reguera ............... C25B 15/08 |
| 2007/0042480 A1 | 2/2007 | Rozendal et al. |
| 2008/0090736 A1 | 4/2008 | Zhao et al. |
| 2008/0124585 A1 | 5/2008 | Schilling |
| 2009/0017512 A1 | 1/2009 | May et al. |
| 2009/0142627 A1 | 6/2009 | Shimomura et al. |
| 2009/0253190 A1 | 10/2009 | Chidambaram |
| 2009/0286294 A1 | 11/2009 | Blanchard et al. |
| 2010/0059436 A1 | 3/2010 | Lovley et al. |
| 2010/0304420 A1 | 12/2010 | Gray |
| 2011/0008489 A1 | 1/2011 | Robb et al. |
| 2011/0315560 A1 | 12/2011 | Rabaey et al. |
| 2013/0130334 A1 | 5/2013 | Reguera et al. |
| 2015/0233001 A1 | 8/2015 | Reguera et al. |

FOREIGN PATENT DOCUMENTS

| EP | 2548255 A2 | 1/2013 |
| WO | 2011116185 A2 | 9/2011 |
| WO | 2011116185 A3 | 9/2011 |

OTHER PUBLICATIONS

Final Office Action received for U.S. Appl. No. 14/705,766, dated Feb. 20, 2018, 20 pages.

(Continued)

*Primary Examiner* — Susan E. Fernandez
(74) *Attorney, Agent, or Firm* — Westman, Champlin & Koehler, P.A.

(57) ABSTRACT

An electrochemical cell comprising an anode electrode, a cathode electrode and a reference electrode electronically connected to each other; a first biocatalyst comprising a consolidated bioprocessing organism (e.g., a cellulomonad or *clostridium* or related strains, such as *Cellulomonas uda* (*C. uda*), *Clostridium lentocellum* (*C. lentocellum*), *Acetivibrio celluloyticus* (*A. cellulolyticus*) *Clostridium cellobioparum* (*C. cellobioparum*), alcohol-tolerant *C. cellobioparum*, alcohol-tolerant *C. uda*, and combinations thereof) capable of fermenting biomass (e.g., cellulosic biomass or glycerin-containing biomass) to produce a fermentation byproduct; and a second biocatalyst comprising an electricigen (e.g., *Geobacter sulfurreducens*) capable of transferring substantially all the electrons in the fermentation byproduct (e.g., hydrogen, one or more organic acids, or a combination thereof) to the anode electrode to produce electricity is disclosed. Systems and methods related thereto are also disclosing a consolidated bioprocessing organism.

22 Claims, 12 Drawing Sheets

(56) References Cited

OTHER PUBLICATIONS

Non-Final Office Action received for U.S. Appl. No. 14/705,766, dated Jun. 30, 2017, 17 pages.

Notice of Allowance received for U.S. Appl. No. 14/705,766, dated Apr. 23, 2018, 13 pages.

Ishii, et al., Methanogenesis versus Electrogenesis: Morphological and Phylogenetic Comparisons of Microbial Communities, Bioscience, Biotechnology, and Biochemistry, 2008, pp. 286-294, vol. 72, No. 2.

Ren, et al., Characterization of the cellulolytic and hydrogen-producing activities of six mesophilic Clostridium species, Journal of Applied Microbiology, 2007, pp. 2258-2266, vol. 103.

Extended European Search Report received for European Patent Application No. 11756992.1, dated Oct. 14, 2013, 6 pages.

Office Action received for European Patent Application No. 11756992.1, dated Jan. 4, 2013, 1 page.

Office Action received for European Patent Application No. 11756992.1, dated Jul. 27, 2012, 3 pages.

Non Final Office Action received for U.S. Appl. No. 13/635,137, dated Feb. 18, 2015, 20 pages.

Advisory Action received for U.S. Appl. No. 13/635,137, dated Dec. 7, 2016, 9 pages.

Non Final Office Action received for U.S. Appl. No. 13/635,137, dated Jan. 22, 2016, 17 pages.

Final Office Action received for U.S. Appl. No. 13/635,137, dated Sep. 9, 2015, 18 pages.

Final Office Action received for U.S. Appl. No. 13/635,137, dated Aug. 8, 2016, 23 pages.

Notice of Allowance received for U.S. Appl. No. 13/635,137, dated Mar. 10, 2017, 11 pages.

Restriction Requirement received for U.S. Appl. No. 13/635,137, dated Oct. 20, 2014, 10 pages.

Restriction Requirement received for U.S Appl. No. 14/705,766, dated Jan. 11, 2017, 10 pages.

Office Action received for Canadian Patent Application No. 2,793,194, dated Dec. 16, 2013, 3 pages.

First Examiner Report received for Australian Patent Application No. 2011227256, dated May 22, 2014, 8 pages.

Bond, et al., "Electricity Production by Geobacter sulfurreducens Attached to Electrodes", Applied and Environmental Microbiology, Mar. 2003, pp. 1548-1555, vol. 69, No. 3, American Society for Microbiology.

Cavedon, et al., "Cellulase System of a Free-Living, Mesophilic Clostridium (Strain C7)", Journal of Bacteriology, Aug. 1990, pp. 4222-4230, vol. 172, No. 8, American Society for Microbiology.

Collins, et al., "The Phylogeny of the Genus Clostridium: Proposal of Five New Genera and Eleven New Species Combinations", International Journal of Systematic Bacteriology, Oct. 1994, pp. 812-826, vol. 44, No. 4, International Union of Microbiological Societies.

Coppi, et al., "Development of a Genetic System for Geobacter sulfurreducens", Applied and Environmental Microbiology, Jul. 2001, pp. 3180-3187, vol. 67, No. 7, American Society of Microbiology.

Dermoun, et al., "Effects of End-Product Inhibition of Cellulomonas uda Anaerobic Growth on Cellobiose Chemostat Culture", Journal of Bacteriology, Jun. 1988, pp. 2827-2831, vol. 170, No. 6, American Society of Microbiology.

Fuji, et al., "One-Step random mutagenesis by error-prone rolling circle amplification", Nucleic Acids Research, Oct. 26, 2004, 5 pages, vol. 32, No. 19, e145, Oxford University Press.

The Molecular Probes Handbook—A Guide to Fluorescent Probes and Labeling Technologies, 2010, 8 pages, Available at: lifetechnologies.com/mpeducate.

Heap, et al., "The ClosTron: A universal gene knock-out system for the genus Clostridium", Journal of Microbiological Methods, 2007, vol. 70, pp. 452-464, Science Direct, Elsevier, Available at: www.elsevier.com/locate/jmicmeth.

Heap, et al., "The ClosTron: Mutagenesis in Clostridium refined and streamlined". Journal of Microbiological Methods, 2010, vol. 80, pp. 49-55, Science Direct, Elsevier, Available at: www.elsevier.com/locate/jmicmeth.

Kim, et al., "Mini Review: Simultaneous consumption of pentose and hexose sugars: an optimal microbial phenotype for efficient fermentation of lignocellulosic biomass", Appl Microbiol Biotechnol, 2010, pp. 1077-1085, vol. 88, Springer.

Krahulec, et al., "Research: Fermentation of mixed glucose-xylose substrates by engineered strains of Saccharomyces cerevisiae: role of the coenzyme specificity of xylose reductase, and effect of glucose on xylose utilization", Microbiol Cell Factories, 2010, 14 pages, vol. 9, No. 16.

Lau, et al., "Cellulosic ethanol production from AFEX-trealed corn stover using Saccharomyces cerevisiae 424A(LNH-ST)", PNAS, Feb. 3, 2009, pp. 1368-1373, vol. 106, No. 5, The National Academy of Sciences of the USA, Available at: www.pnas.org/doi/10.1073/pnas.0812364106.

Logan, et al., "Microbial Challenges and Fuel Cell Applications", Environmental Science & Technology, Sep. 1, 2006, pp. 5172-5180, American Chemical Society.

Lovley, et al., "Electricity Production with Electricigens", Bioenergy, 2008, Chapter 23, pp. 295-306, ASM Press.

Lovley, et al., Novel Mode of Microbial Energy Metabolism: Organic Carbon Oxidation Coupled to Dissimilatory Reduction of Iron or Manganese, Applied and Environmental Microbiology, Jun. 1988, pp. 1472-1480, vol. 54, No. 6, American Society of Microbiology.

Marschoun, et al., "Metabolism of hexoses and pentoses by Cellulomonas uda under aerobic conditions and during fermentation", Can. J. Microbial, 1987, pp. 1024-1031, vol. 33.

Marsili, et al., "Microbial Biofilm Voltammetry: Direct Electrochemical Characterization of Catalytic Electrode-Attached Biofilms", Applied and Environmental Microbiology, Dec. 2008, pp. 7329-7337, vol. 74, No. 23, American Society for Microbiology.

Moon, et al., "Effect of Biodiesel-derived Raw Glycerol on 1,3-Propanediol Production by Different Microorganisms", Applied Biochemistry and Biotechnology, 2010, pp. 502-510, vol. 161, Springer Science.

Office Action received for Mexican Patent Application No. MX/a/2012/010670, dated Jul. 1, 2015, 3 pages.

Office Action received for Mexican Patent Application No. MX/a/2012/010670, dated Jun. 1, 2016, 4 pages.

Office Action received for Mexican Patent Application No. MX/a/2012/010670, dated Nov. 23, 2015, 6 pages.

Park, et al., "Improved Fuel Cell and Electrode Designs for Producing Electricity from Microbial Degradation", Jul. 16, 2002, pp. 348-355, Wiley Periodicals, Inc.

International Search Report and Written Opinion received for PCT Patent Application No. PCT/US2011/028807, dated Nov. 25, 2011, 8 pages.

Written Opinion received for PCT Patent Application No. PCT/US20111028807, dated Nov. 25, 2011, 5 pages.

Reguera, et al., "Consolidated Bioprocessing Technologies using Microbial Fuel Cells Powered by Microbial Consortia", CERMACS, Central Regional Meeting of the American Chemical Society, May 20-23, 2009, 36 pages.

Ren, et al., "Electricity Production from Cellulose in a Microbial Fuel Cell Using a Defined Binary Culture", Environ. Sci. Technol., 2007, pp. 4781-4786, vol. 41, No. 13, American Chemical Society.

Shao, et al., "A High-Molecular-Weight, Cell-Associated Xylanase Isolated from Exponentially Growing Thermoanaerobacterium sp. Strain JW/SL-YS485", Applied and Environmental Microbiology, Mar. 1995, pp. 937-940, vol. 61, No. 3, American Society for Microbiology.

Shin, et al., "Electrically enhanced ethanol fermentation by Clostridium thermocellum and Saccharomyces cerevisiae", Applied Microbiology and Biotechnology, 2002, pp. 476-481, vol. 58, Springer-Verlag.

Speers, et al., "Fermentation of Glycerol into Ethanol in a Microbial Electrolysis Cell Driven by a Customized Consortium", Environmental Science & Technology, 2014, pp. 6350-6358, vol. 48, American Chemical Society.

(56) References Cited

OTHER PUBLICATIONS

Speers, et al., "Consolidated Bioprocessing of AFEX-Pretreated Corn Stover to Ethanol and Hydrogen in a Microbial Eletrolysis Cell", Environmental Science & Technology, Jun. 14, 2012, American Chemical Society, 7 pages.
Speers, et al. "Direct Conversion of Glycerol into Electricity for Wastewater Treatment and Energy Recovery in the Biodiesel Industry", Department of Microbiology and Molecular Genetics, prior to May 8, 2017, 1 page.
Speers, et al., "Electron Donors Supporting Growth and Electroactivity of *Geobacter sulfurreducens* Anode Biofilms", Journals.ASM. org, Applied and Environmental Microbiology, Jan. 2012, pp. 437-444, vol. 78, No. 2.
Suehara, et al., "Biological Treatment of Wastewater Discharged from Biodiesel Fuel Production Plant with Alkali-Catalyzed Transesterification", Journal of Bioscience and Bioengineering, 2005, pp. 437-442, vol. 100, No. 4, The Society for Biotechnology.
Tompkins, et al., "Error-Prone Polymerase, DNA Polymerase IV, Is Responsible for Transient Hypermutation during Adaptive Mutation in *Escherichia coli*", Journal of Bacteriology, Jun. 2003, pp. 3469-3472, vol. 185, No. 11.
U.S. Department of Energy, Joint Meeting, Genomics: GTL Awardee Workshop VII and USDA-DOE Plant Feedstock Genomics for Bioenergy Awardee Workshop 2009, Feb. 8-11, 2009, 232 pages, Available at: http://genomicsgtl.energy.gov.
Warnick, et al., "*Clostridium phytofermentans* sp. nov., a cellulolytic mesophile from forest soil", International Journal of Systematic and Evolutionary Microbiology. 2002, pp. 1155-1160, vol. 52, IUMS.
Williams, et al., "Critical Review: Environmental and Sustainability Factors Associated with Next-Generation Biofuels in the U.S.: What Do We Really Know?", Environmental Science & Technology, 2009, pp. 4763-4775, vol. 43, No. 13, American Chemical Society.
Yazdani, et al., "Anaerobic fermentation of glycerol: a path to economic viability for the biofuels industry", Elsevier, Science Direct, Current Opinion in Biotechnology, 2007, pp. 213-219. vol. 18, Available at: www.sciencedirect.com.
Office Action received for Mexican Patent Application No. MX/a/2012/010670, dated May 9, 2016, 4 pages (English Translation Only).
Biomass Feedstocks, Office of Efficiency & Renewable Energy, www.energy.gov/eere/bioenergy/biomass-feedstocks, 6 pages, Jul. 23, 2019.
Summers, Genomics: GTL Contractor-grantee workshop VII (ed. Office of Science U.S. Dept of Energy)(Genome Management information system (Oak Ridge National Laboratory)), 29 pages, 2009.
Office Action received from Mexican Patent Application No. MX/a/2012/010670, dated Oct. 30, 2015, 6 pages (English Translation Only).
Office Action received for Mexican Patent Application No. MX/a/2012/010670, date May 9, 2016, 4 pages (English Translation Only).
Phillips-Jones, Introduction of Recombinant DNA into *Clostridium* spp., Methods in Molecular Biology, vol. 47: Electroporation Protocols for Microorganisms, pp. 227-235, 1995.

\* cited by examiner

BIOFUEL AND ELECTRICITY PRODUCING FUEL CELLS AND SYSTEMS AND METHODS RELATED TO SAME

This application is a Divisional of U.S. application Ser. No. 13/635,137, filed on Dec. 28, 2012, which application is a U.S. National Stage Filing under 35 U.S.C. 371 from International Application No. PCT/US2011/028807, filed Mar. 17, 2011, and published in English as WO WO/2011/116185 on Sep. 22, 2011, which claims the benefit under 35 U.S.C. 119 (e) of U.S. Provisional Application Ser. No. 61/314,936 filed on Mar. 17, 2010, which applications and publications are hereby incorporated by reference in their entireties.

BACKGROUND

The increased concern for the inevitable depletion of the oil supply as well as the negative impact of the use of fossil fuels on the environment has highlighted the need for biofuel alternatives from renewable resources, such as ethanol, diesel, butanol and hydrogen. Ideally, a biofuel should have a high energy content and be compatible with the current petroleum-based transportation, storage and distribution infrastructures.

The inventors recognize a need in the art for systems and methods that provide for improved biomass conversion to biofuel in a cost-effective manner.

SUMMARY

In one embodiment, a fuel cell comprising an anode electrode, a cathode electrode and a reference electrode electronically connected to each other; a first biocatalyst comprising a consolidated bioprocessing and/or fermentative organism (e.g., a cellulomonad, such as *Cellulomonas uda* (*C. uda*), or a *clostridium* such as *Clostridium lentocellum* (*C. lentocellum*), *Clostridium cellobioparum* (*C. cellobioparum*), adaptively evolved strains of such organisms, such as alcohol-tolerant strains, glycerol-tolerant strains, heat-tolerant strains and combinations thereof) capable of processing and fermenting biomass (e.g., cellulosic-containing, polyol-containing, such as glycerin-containing water, etc.) to produce a biofuel and fermentation byproducts; and a second biocatalyst comprising an electricity-producing microorganism or electricigen (e.g., *Geobacter sulfurreducens*, (Gsu) or alcohol-tolerant Gsu (GsuA)) capable of transferring substantially all the electrons in the fermentation byproducts (e.g., hydrogen, one or more organic acids, or a combination thereof) to the anode electrode to produce electricity.

In one embodiment, the biomass is cellulosic biomass. In one embodiment, the biomass is a polyol, such as glycerin-containing water.

In one embodiment, the fuel cell further comprises an exchange membrane capable of transferring electrons and protons; and an electronic device connected to the anode electrode, the cathode electrode and the reference electrode.

In one embodiment, the anode electrode, the cathode electrode and the reference electrode are located in a single chamber. In one embodiment, the anode electrode and the reference electrode are located in a first chamber and the cathode electrode is located in a second chamber.

In one embodiment, the fermentation byproduct is primarily hydrogen.

In one embodiment, the consolidated bioprocessing (CBP) organism comprises one or more cellulomonads, such as *Cellulomonas uda* (Cuda), or clostridial or a clostridial-related strain, such as *C. lentocellum* or *Acetivibrio cellulolyticus*. In one embodiment, the CBP organism comprises *A. Acellulolyticus, C. cellobioparum* (Cce) or a combination thereof. In one embodiment the Cce is a glycerol- or alcohol-tolerant strain of Cce (CceA) or a combination thereof. In one embodiment, alcohol tolerance is evolved in any of the aforementioned CBP organisms to produce an alcohol-tolerant strain of the CBP organism to improve performance of the biocatalyst (e.g., alcohol-tolerant Cuda).

Embodiments further include a system comprising a biofuel production facility configured to produce a biofuel (e.g., ethanol, biodiesel fuel) and a biomass waste stream (e.g., cellulosic-containing biomass waste stream, glycerin-containing biomass wastestream), wherein the biofuel is produced from biomass; a fuel cell system configured to produce alcohol and electricity from the biomass waste stream, the fuel cell system comprising an anode electrode, a cathode electrode and a reference electrode electronically connected to each other; a first biocatalyst comprising a consolidated bioprocessing organism capable of fermenting biomass to produce a fermentation byproduct; and a second biocatalyst comprising an electricigen capable of transferring substantially all the electrons in the fermentation byproduct to the anode electrode to produce electricity. In one embodiment, the system further comprises a computer system connected to the fuel cell for monitoring and controlling fuel cell activity.

In one embodiment, the electrodes are housed in a single chamber or a double chamber as described above.

Embodiments further include a method comprising, a consolidated hydrolyzing and fermentation step for converting biomass to a biofuel with a first organism in an anode chamber, wherein the anode reactor contains an anode electrode and the converting step produces a fermentation byproduct; transferring electrons in the byproduct to the anode electrode with a second organism to produce a film, and allowing the film to catalytically split the electrons and protons, wherein the electrons flow towards a cathode electrode to produce electricity and the protons permeate a proton-exchange membrane connecting the anode chamber and the cathode chamber, wherein the electrons and protons react to produce hydrogen gas.

In one embodiment, the first and second organisms are added sequentially. In one embodiment, the first and second organisms are added substantially simultaneously.

In one embodiment, the method further comprises applying a potential to the anode electrode.

In one embodiment, the biofuel is ethanol. In one embodiment, the ethanol is produced in less than 50 hours at a yield greater than 40% of a total theoretical yield. In one embodiment, the biofuel is biodiesel fuel.

In one embodiment, biomass conversion to biofuel is catalyzed by a consolidated bioprocessing organism, thus reducing the cost associated with enzymatic hydrolysis. In various embodiments, fermentation products other than the biofuel (i.e., fermentation byproducts, typically considered to be a waste byproduct) are removed by a second organism, i.e., an electricigen, which converts the fermentation byproducts into electricity, thus producing an added-value product. This step also prevents media acidification and accumulation of feedback inhibitors and toxic byproducts, thereby improving hydrolysis and fermentation efficiency.

The biomass may, in some embodiments, be a non-food biomass, such as corn stover or glycerin-containing water.

DETAILED DESCRIPTION

Figure 1:
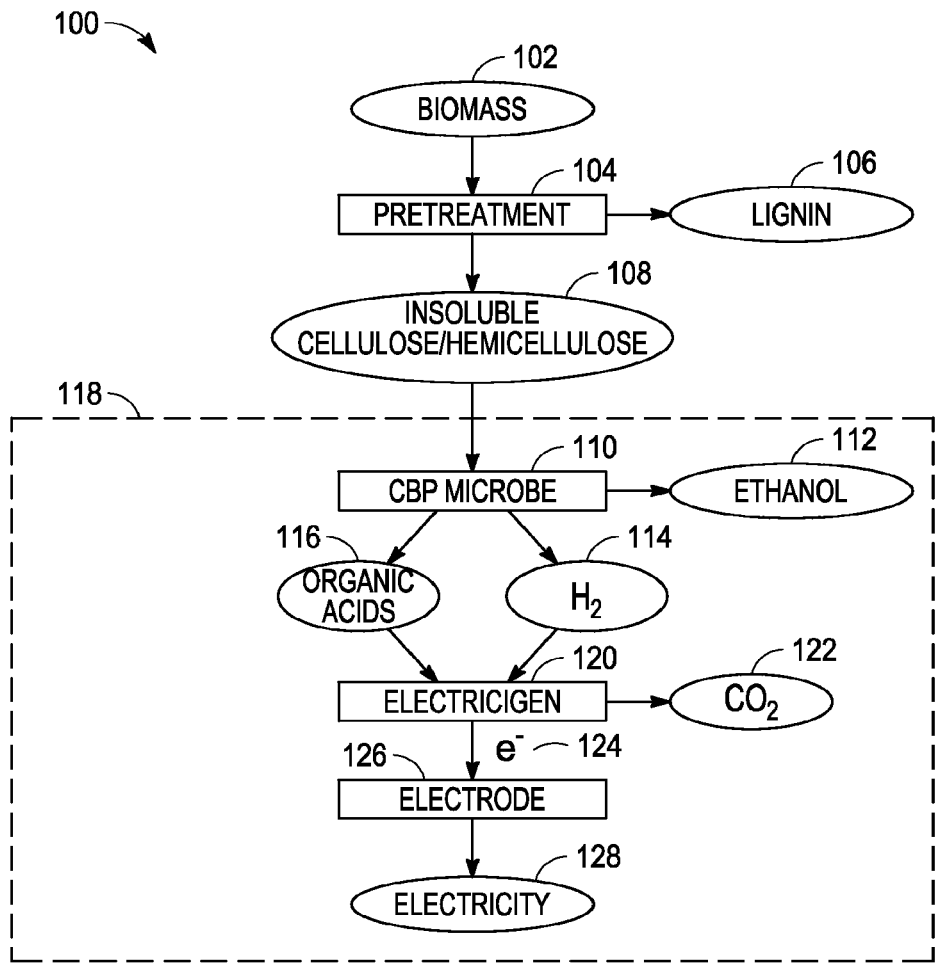
FIG. 1 is a simplified schematic of a consolidated process for ethanol and electricity generation according to an embodiment.

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

In one embodiment, a consolidated bioprocessing technology in a bioelectrochemical cell (BEC), such as a microbial fuel cell (MFC), is driven by first and second microbial partners. The first microbial partner can be a consolidated bioprocessing (CBP) organism, as defined herein. In one embodiment, the CBP organism degrades a lignocellulosic substrate and further co-ferments substantially all the fermentation sugars into ethanol and fermentation byproducts. In one embodiment, the lignocellulosic substrate is pretreated, such as chemically pretreated. In one embodiment, the CBP organism degrades a polyol, such as glycerin-containing water. The second microbial partner can be an electricigen, as defined herein. In one embodiment, *Geobacter sulfurreducens* (Gsu) serves as the electricigen.

The Detailed Description that follows begins with a definition section followed by a brief overview of current technologies for production of alcohol (both grain-based and cellulosic-based), a description of the embodiments, an example section and a brief conclusion.

Definitions

The term "biomass" as used herein, refers in general to organic matter harvested or collected from a renewable biological resource as a source of energy. The renewable biological resource can include plant materials, animal materials, and/or materials produced biologically. The term "biomass" is not considered to include fossil fuels, which are not renewable.

The term "plant biomass" or "lignocellulosic biomass" as used herein, is intended to refer to virtually any plant-derived organic matter (woody or non-woody) available for energy on a sustainable basis. Plant biomass can include, but is not limited to, agricultural crop wastes and residues such as corn stover, wheat straw, rice straw, sugar cane bagasse and the like. Plant biomass further includes, but is not limited to, woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally grass crops, such as various prairie grasses, including prairie cord grass, switchgrass, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States.

The term "biofuel" as used herein, refers to any renewable solid, liquid or gaseous fuel produced biologically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. Biofuels can be derived from biomass synthesized during photosynthesis. These include, for example, agricultural biofuels (defined below), such as biodiesel fuel. Biofuels can also be derived from other sources, such as algae, to produce algal biofuels (e.g., biodiesel fuel). Biofuels can also be derived from municipal waste s (residential and light commercial garbage or refuse, with most of the recyclable materials such as glass and metal removed) and from forestry sources (e.g., trees, waste or byproduct streams from wood products, wood fiber, and pulp and paper industries). Biofuels produced from biomass not synthesized during photosynthesis also include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "biodiesel fuel" or "biodiesel" as used herein, refers generally to long-chain ($C_{12}$-$C_{22}$) fatty acid alkyl esters, which can be either fatty acid methyl (FAMEs) or ethyl (FAEEs) esters. Biodiesel fuel can be produced from both agricultural and algal oil feedstocks. Biodiesel fuel is chemically analogous to petrochemical diesel, which fuels compression engines and can be mixed with petrodiesel to run conventional diesel engines. Petrodiesel is a fuel mixture of $C_9$ to $C_{23}$ hydrocarbons of average carbon length of 16, having approximately 75% of linear, branched, and cyclic alkanes and 25% aromatic hydrocarbons. In general, biodiesel and petrodiesel fuels have comparable energy content, freezing temperature, vapor pressure, and cetane rating. Biodiesel fuel also has higher lubricity and reduced emissions. The longer chain in FAEEs increases the cetane rating and energy content of the fuel, while decreasing its density, and pour and cloud points. As a result, combustion and flow properties (including cold flow properties) are improved, as is fuel efficiency. Once combusted, emissions and smoke densities are also minimized.

The term "agricultural biofuel", as used herein, refers to a biofuel derived from agricultural crops (e.g., grains, such as corn), crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "glycerin-containing water", as used herein, refers to a liquid, such as water, containing any amount of glycerin (i.e., glycerol, a polyol). The liquid can contain other components, such as solids, alcohols, oils, salts and/or other components. Glycerin-containing water includes glycerin wastewater produced as a waste product of biodiesel fuel production or from ethanol biorefineries. Although glycerin wastewater can refer to either "crude glycerin wastewater" (i.e., "unrefined glycerin wastewater" which is glycerin wastewater in its initial state after separation from a biodiesel fuel product) or "refined glycerin wastewater" following treatment (typically in preparation for selling) which increases the volume of glycerin to at least about 80% by volume, the processes described herein are useful with crude glycerin water, thus eliminating the need for refining glycerin wastewater in the conventional manner.

The term "biodegradable", as used herein, refers to a substrate capable of being decomposed, i.e., chemically broken down, by the action of one or more biological agents, such as bacteria.

The term "electricigen" as used herein, refers to a biocatalyst which is electrochemically active or an electricity-generating microorganism, i.e., an organism capable of transferring electrons to an electrode with or without mediators.

The term "bioprocessing microorganism" as used herein, refers to a microorganism capable of degrading biomass, such as lignocellulosic biomass.

The term "consolidated bioprocessing (CBP) organism" as used herein refers to a biocatalyst which is also capable of fermenting the degraded biomass into one or more biofuels, i.e., capable of performing a single step hydrolysis and fermentation.

The term "alcohol-tolerant" as used herein, refers to a mutant of a microbial strain adaptively evolved or genetically engineered to have increased tolerance to alcohol as compared with the native microbe.

The term "glycerol-tolerant" as used herein, refers to a mutant of a microbial strain adaptively evolved or genetically engineered to have an increased tolerance to glycerol as compared with the native microbe.

The term "heat-tolerant" as used herein, refers to a mutant of a microbial strain adaptively evolved or genetically engineered to have an increased tolerance to heat as compared with the native microbe.

The term "adaptive evolution" as used herein, refers to the process that enhances the fitness of an organism to a particular environmental condition under appropriate selective pressure.

The term "ethanologenesis", as used herein, refers to the metabolic process that results in the production of ethanol.

The terms "fuel cell" or "electrochemical cell", as used herein, refer to a device used for the generation of electricity from a chemical or microbial reaction. The reaction can proceed naturally or can be facilitated with electrical input from, for example, a potentiostat. A fuel cell is comprised of anode and cathode electrodes connected through a conductive material. The electrodes may be housed in a single or double, i.e., separate chamber and when housed in a double, i.e., separate chamber, may be separated by a cation- or proton-exchange membrane. A chemical or biological catalyst added to the anode drives electricity generation.

The term "microbial fuel cell" or "microbial electrochemical cell" as used herein, refers to a fuel cell driven by electricigenic microorganisms either in a substantially pure (i.e., at least 90% purity) culture of at least a single species or in a mixed-species culture, i.e., a co-culture, which can include the electricigen at any concentration and a number of other species or as part of microbial consortia, i.e., a group of different species of microorganisms which may have different metabolic capabilities, but which act together as a community, such as a natural (e.g., biofilms) or defined laboratory microbial consortia.

The term "bioelectrochemical cell" or "BEC" as used herein, refers to an MFC capable of inputting additional voltage to control product outputs of the system and increase its performance.

The term "bioelectricity" as used herein, refers to electricity produced biologically, e.g., from biological materials such as biofuels and biomass.

The term "pretreatment step" as used herein, refers to any step intended to alter native biomass so it can be more efficiently and economically converted to reactive intermediate chemical compounds such as sugars, organic acids, etc., which can then be further processed to a variety of value added products such a value-added chemical, such as ethanol. Pretreatment can reduce the degree of crystallinity of a polymeric substrate, reduce the interference of lignin with biomass conversion and prehydrolyze some of the structural carbohydrates, thus increasing their enzymatic digestibility and accelerating the degradation of biomass to useful products. Pretreatment methods can utilize acids of varying concentrations (including sulfuric acids, hydrochloric acids, organic acids, etc.) and/or other components such as ammonia, ammonium, lime, and the like. Pretreatment methods can additionally or alternatively utilize hydrothermal treatments including water, heat, steam or pressurized steam. Pretreatment can occur or be deployed in various types of containers, reactors, pipes, flow through cells and the like. Most pretreatment methods will cause the partial or full solubilization and/or destabilization of lignin and/or hydrolysis of hemicellulose to pentose sugars.

The term "moisture content" as used herein, refers to percent moisture of biomass. The moisture content is calculated as grams of water per gram of wet biomass (biomass dry matter plus water) times 100%.

The term "Ammonia Fiber Explosion" or "Ammonia Fiber Expansion" (hereinafter "AFEX") pretreatment" as used herein, refers to a process for pretreating biomass with ammonia to solubilize lignin and redeposit it from in between plant cell walls to the surface of the biomass. An AFEX pretreatment disrupts the lignocellulosic matrix, thus modifying the structure of lignin, partially hydrolyzing hemicellulose, and increasing the accessibility of cellulose and the remaining hemicellulose to subsequent enzymatic degradation. Lignin is the primary impediment to enzymatic hydrolysis of native biomass, and removal or transformation of lignin is a suspected mechanism of several of the leading pretreatment technologies, including AFEX. However in contrast to many other pretreatments, the lower temperatures and non-acidic conditions of the AFEX process prevents lignin from being converted into furfural, hydroxymethyl furfural, and organic acids that could negatively affect microbial activity. The process further expands and swells cellulose fibers and further breaks up amorphous hemicellulose in lignocellulosic biomass. These structural changes open up the plant cell wall structure enabling more efficient and complete conversion of lignocellulosic biomass to value-added products while preserving the nutrient value and composition of the material. See, for example, the methods described in U.S. Pat. Nos. 6,106,888, 7,187,176, 5,037,663, and 4,600,590, all of which are hereby incorporated by reference in their entirety as if fully set forth herein.

Grain-Based Alcohol

The methods for producing various types of alcohol from grain generally follow similar procedures, depending on whether the process is operated wet or dry. One alcohol of great interest today is ethanol. Ethanol can be produced from virtually any type of grain, but is most often made from corn. Corn contains high levels of starches that can be broken down into the glucose sugars needed for traditional fermentation.

The corn grain may be chemically pretreated, as is known in the art, to increase its enzymatic digestibility. Thereafter, the pretreated corn grain is hydrolyzed into soluble sugars by microbial enzyme mixtures. The resulting soluble sugars are only partially fermented by genetically engineered strains of bacteria or fungi. Fermentation is also limited by acidification of the media, due, in part, to the production of organic acids during microbial fermentative metabolism. Fermentation is also limited by feedback inhibition on the microbial metabolism from fermentation byproducts such as hydrogen gas and organic acids.

The resulting ethanol is then distilled and evaporated for separation from the remaining fermentation products. The solid biomass waste material is filtered and washed to separate the lignin waste from the remaining biomass waste. Optimization efforts have focused on genetically engineering microbes for degrading and fermenting the biomass substrate, cellulase improvement by direct evolution, and/or engineering industrial strains with more efficient and stable cellulase and hemicellulase enzymes, with only moderate success. However, production of alcohols (e.g., ethanol) using grain is gradually being replaced with other, more efficient and sustainable solutions. Of note, production of ethanol as described above, also generates a glycerol byproduct at concentrations up to about 10% (w/w) of the total sugar consumed.

Biomass Conversion to Alcohol

Nearly all forms of lignocellulosic biomass, i.e., plant biomass, such as monocots, comprise three primary chemical fractions: hemicellulose, cellulose, and lignin. Hemicellulose is a polymer of short, highly-branched chains of mostly five-carbon pentose sugars (xylose and arabinose), and to a lesser extent six-carbon hexose sugars (galactose, glucose and mannose). Dicots, on the other hand, have a high content of pectate and/or pectin, which is a polymer of alpha-linked glucuronic acid. Pectate may be "decorated" with mannose or rhamnose sugars, also). These sugars are highly substituted with acetic acid.

Because of its branched structure, hemicellulose is amorphous and relatively easy to hydrolyze (breakdown or cleave) to its individual constituent sugars by enzyme or dilute acid treatment. Cellulose is a linear polymer of glucose sugars, much like starch, which is the primary substrate of corn grain in dry grain and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Lignin, which is a polymer of phenolic molecules, provides structural integrity to plants, and remains as residual material after the sugars in plant biomass have been fermented to ethanol. Lignin is a by-product of alcohol production and is considered a premium quality solid fuel because of its zero sulfur content and heating value, which is near that of sub-bituminous coal.

Typical ranges of hemicellulose, cellulose, and lignin concentrations in plants are shown in http://www1.eere.energy.gov/biomass/feedstock_databases.html. Typically, cellulose makes up 30 to 50% of residues from agricultural, municipal, and forestry sources. Cellulose is more difficult to hydrolyze than hemicellulose, but, once hydrolyzed, converts more efficiently into ethanol with glucose fermentation than hemicellulose. In contrast, the sugar polymers of hemicellulose are relatively easy to hydrolyze, but do not convert as efficiently as cellulose using standard fermentation strains (which produce ethanol from glucose). Although hemicellulose sugars represent the "low-hanging" fruit for conversion to ethanol, the substantially higher content of cellulose represents the greater potential for maximizing alcohol yields, such as ethanol, on a per ton basis of plant biomass.

Conventional methods used to convert biomass to alcohol include processes employing a concentrated acid hydrolysis pretreatment, a two-stage acid hydrolysis pretreatment as well as processes employing any known conventional pretreatment, such as hydrothermal or chemical pretreatments, followed by an enzymatic hydrolysis (i.e., enzyme-catalyzed hydrolysis) or simultaneous enzymatic hydrolysis and saccharification. Such pretreatment methods can include, but are not limited to, dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), AFEX, ammonia recycled percolation (ARP), lime treatment and a pH-based treatment. However, pretreatment-hydrolysis of plant biomass can often result in the creation and release of other chemicals that inhibit microbial fermentation. These inhibitors (i.e. furfural) are largely the product of sugar degradation, and methods to remove these inhibitors or to reduce their formation or strains resistant to the inhibitors are needed.

Several of these methods generate nearly complete hydrolysis of the hemicellulose fraction to efficiently recover high yields of the soluble pentose sugars. However, chemical solubilization of hemicellulose also produces toxic products, such as furan derivatives, which can inhibit downstream microbial reactions (e.g., fermentation). Regardless, the hydrolysis of hemicellulose facilitates the physical removal of the surrounding hemicellulose and lignin, thus exposing the cellulose to later processing. However, most, if not all, pretreatment approaches do not significantly hydrolyze the cellulose fraction of biomass.

Biomass conversion to alcohol also poses unique fermentation considerations. The *Saccharomyces cerevisiae* yeast strains used in conventional corn ethanol plants for example, can ferment glucose, but cannot ferment pentose sugars such as xylose. Additionally, there is currently no naturally-occurring microorganism that can effectively convert all the major sugars present in plant biomass to ethanol. Therefore, genetically engineered yeast or bacteria, which can, in theory, ferment both glucose and xylose to alcohol, are being used for biomass to alcohol processes. However, in practice, co-fermentation in this manner is inefficient and glucose fermentation is still the main reaction for ethanol production. Furthermore, genetically-enhanced recombinant strains of fermentative microorganisms, including recombinant strains of yeast, bacteria and fungi, as well as transgenic nucleic acids (DNA, RNA) derived from such components may pose environmental disposal and permitting problems.

Biodiesel Fuel Production

Biodiesel fuel (hereinafter "biodiesel") is typically produced via transesterification of triglycerides using an alcohol and catalyst. In the presence of the catalyst, the alcohol reacts with the oil's triglycerides and sequentially removes one methyl ester at a time to generate biodiesel fatty acid esters and glycerol as shown in the reaction below:

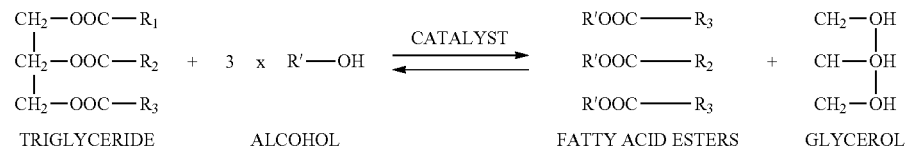

Biodiesel's fatty acid esters have variable lengths and bonds corresponding to the side chains of the triglycerides in the starting oil, with the most frequent being palmitate (C16:0), stearic acid (C18:0), oleic acid (C18:1), linoleic acid (C18:2), and linolenic acid (C18:3) in different proportions. Although acid and alkali catalysts can be used for the transesterification reaction, many commercial biodiesel producers use alkaline catalysts, which are less corrosive and have a higher (about 4,000 times) reaction rate. Inexpensive alkaline catalysts such as sodium and potassium hydroxide are commonly used at concentrations between about 0.5% and about 1% to achieve yields of biodiesel ranging from about 94 to about 99%.

Methanol and ethanol are the most common alcohols used in the transesterification reaction and produce, respectively, fatty acid methyl esters (FAMEs) and fatty acid ethyl esters (FAEEs). As compared to methanol, ethanol is more biodegradable and has a lower toxicity. Ethanol further has a higher solubility as compared to methanol, allowing for higher reaction temperatures and increases in the reaction rate.

Figure 14:
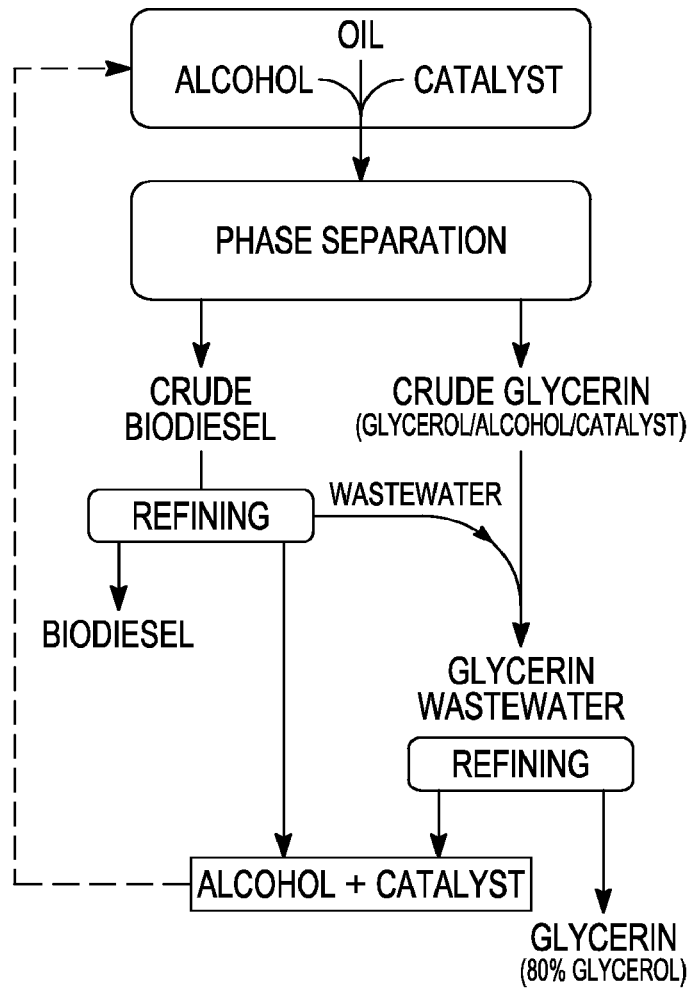
FIG. 14 is a simplified schematic diagram showing a process for producing biodiesel fuel.

As shown in FIG. 14, biodiesel production involves not only transesterification, but also separation of the crude biodiesel from glycerin waste, and biodiesel refining. In an example biodiesel production process, transesterification can proceed in a reactor for about 1-2.5 hrs at about 60 to about 80° C. to generate an approximately 10:90 mixture of crude glycerin (i.e., a mixture of glycerol, alcohol, catalyst and oil impurities) and crude biodiesel. The higher density of crude glycerin enables a phase separation in a settling tank or a centrifuge. Water can be added to the mix to improve the phase separation, thus generating a crude glycerin stream of roughly about 40-50% glycerol, together with some alcohol, oils, most of the catalyst, and soap.

Crude biodiesel also contains impurities (primarily soap and catalyst, together with alcohol), and is typically further refined. The alcohol, for example, can be removed with water, thus producing high-quality biodiesel. Thereafter, the washed wet biodiesel is allowed to dry, such as by a vacuum flash process, while the wastewater, containing alcohol, salts and glycerol, is removed by suitable means, such as with centrifugation, and added to the crude glycerin waste. This step further dilutes the concentration of glycerol in the glycerin wastewater to ca. 10-20% with an average alcohol content of 5%.

Glycerin wastewater is the major waste product of the biodiesel industry and can pose environmental concerns, as it is generally not cost effective to refine and concentrate the glycerol in the wastewater to sell to glycerol refineries. As FIG. 14 shows, prior to selling glycerin wastewater, costly pretreatment and concentration steps are generally undertaken. As such, unrefined glycerin wastewater is oftentimes disposed of as hazardous waste (e.g., containing hazardous concentrations of glycerol and methanol), which can be costly to the biodiesel producer.

As shown in FIG. 14, glycerin wastewater is generally refined prior to selling, to remove oils, alcohol and salts before being concentrated to a purity of approximately 80% glycerol, a concentration generally recognized in the industry as a minimum standard for glycerol feedstock purity. This is a costly process that involves acid pretreatment to remove oils and to neutralize and precipitate the alkali-catalyst and convert the soaps into water-soluble salts and free fatty acids. Even more costly is the stripping of the low concentrations of alcohol from the glycerin solution and its concentration by flash-evaporation or distillation.

Description of the Embodiments

A novel system for producing alcohol and generating electricity in a combined or consolidated process is described herein. In one embodiment, the process involves providing biomass, such as lignocellulosic-containing biomass (such as from an ethanol production facility) or a polyol-containing biomass, such as glycerin-containing water, such as glycerin wastewater (e.g., crude or partially refined glycerin wastewater from a biodiesel production facility).

In the embodiment shown in FIG. 1, a process 100 is provided in which lignocellulosic-containing biomass 102 is subjected to one or more pretreatment steps to separate lignin 106 from insoluble cellulose/hemicellulose (hereinafter "insolubles") 108.

In the embodiment shown in FIG. 1, the insolubles 108 are provided to a microbial fuel cell (MFC) 118 where they are degraded, i.e., hydrolyzed and fermented in a single-step process using a consolidated bioprocessing (CBP) microbe 110 to produce ethanol 112 and fermentation byproducts such as hydrogen gas ($H_2$) 114 and organic acids 116. The hydrogen gas 114 and/or organic acids 116 provide a source of electrons 124 to support the growth of an electricigen 120, which gains energy by transferring electrons 124 to an electrode 126, thereby producing electricity 124 and a carbon dioxide ($CO_2$)-containing waste stream 122.

Unlike conventional cellulosic ethanol processes which require separate hydrolysis and fermentation steps, embodiments described herein provide for use of a CBP organism 110 which is not only capable of catalyzing the enzymatic hydrolysis, but can also serve as an alcohologenic biocatalyst (alcohologenesis). In one embodiment, the CBP organism 110 serves as an alcohologenic biocatalyst (e.g., an ethanologenic biocatalyst). As such, the embodiments described herein are not reliant on a previous biomass solubilization step or previous growth of the CBP organism 110 and electricigen 120 in separate vessels prior to initiation of the fermentation process. This is in contrast with conventional methods in which the electricigenic organism is grown as a pure culture on an electrode of a first fuel cell to produce an electrochemically-active film, which is then transferred to a second fuel cell inoculated with an ethanologenic microbe and supplemented with a biomass hydrolysate. Such steps not only add complexity to the process, they increase costs. Furthermore, the use of ethanologenic microorganisms in conventional methods that produce fermentation byproducts other than those that the electricigen can convert into electricity results in reduced electricity production and feedback inhibition of the fermentation by the CBP organism 110. In embodiments described herein, both the CBP organism 110 and the electricigen 120 can be simultaneously inoculated or sequentially inoculated in the same reactor while maintaining the net production of ethanol and electricity (See Example 3).

Any suitable biomass, as defined herein can be used. In one embodiment, the biomass is a non-food biomass, such as agricultural waste. In one embodiment, corn stover is used. Additional steps known in the art may also be used to prepare the biomass for use in the novel process, including, but not limited to, milling.

The pretreatment step 104 may take the form of any known pretreatment step, including chemical pretreatment. Heating or cooking with added water may also occur, as is known in the art. In a particular embodiment AFEX corn stover as defined herein, is used. Any fuel cell 118 having a suitable configuration and size may be used in the embodiments described herein. In one embodiment, the fuel cell is a microbial fuel cell (MFC), such as the type described in *Microbial Fuel Cells—Challenges and Applications*, Bruce E. Logan and John M. Regan, Environ. Sci. Technol., 2006, 40 (17), pp 5172-5180, which is incorporated herein by reference in its entirety.

In one embodiment, the anode and cathode electrodes are housed in separate chambers. In one embodiment, the anode and cathode electrodes are separated by a cation- or proton-exchange membrane. Spacing between the anode electrode and the cathode electrode can also vary, as is understood by those skilled in the art.

In one embodiment, the anode and cathode electrodes of the fuel cell are housed in the same chamber. See, for example, *Microbial biofilm voltammetry: direct electrochemical characterization of catalytic electrode-attached biofilms*. Marsili E, Rollefson J B, Baron D B, Hozalski R M, Bond D R. Appl Environ Microbiol. 2008 December: 74(23):7329-37. Epub 2008 Oct. 10, which is hereby incorporated by reference in its entirety.

In one embodiment, an external or air-breathing cathode electrode is used. In this embodiment, the cathode chamber is removed and the cathode electrode is placed externally and in direct contact with the proton-exchange membrane. See, for example, *Improved fuel cell and electrode designs for producing electricity from microbial degradation*, Park D H, Zeikus J G. Biotechnol Bioeng. 2003 Feb. 5:81(3): 348-55 and *Electrically enhanced ethanol fermentation by Clostridium thermocellum and Saccharomyces cerevisiae*. Shin H S, Zeikus J G, Jain M K., Appl Microbiol Biotechnol. 2002 March: 58(4):476-81, both of which are incorporated herein by reference in their entireties.

Figure 2:
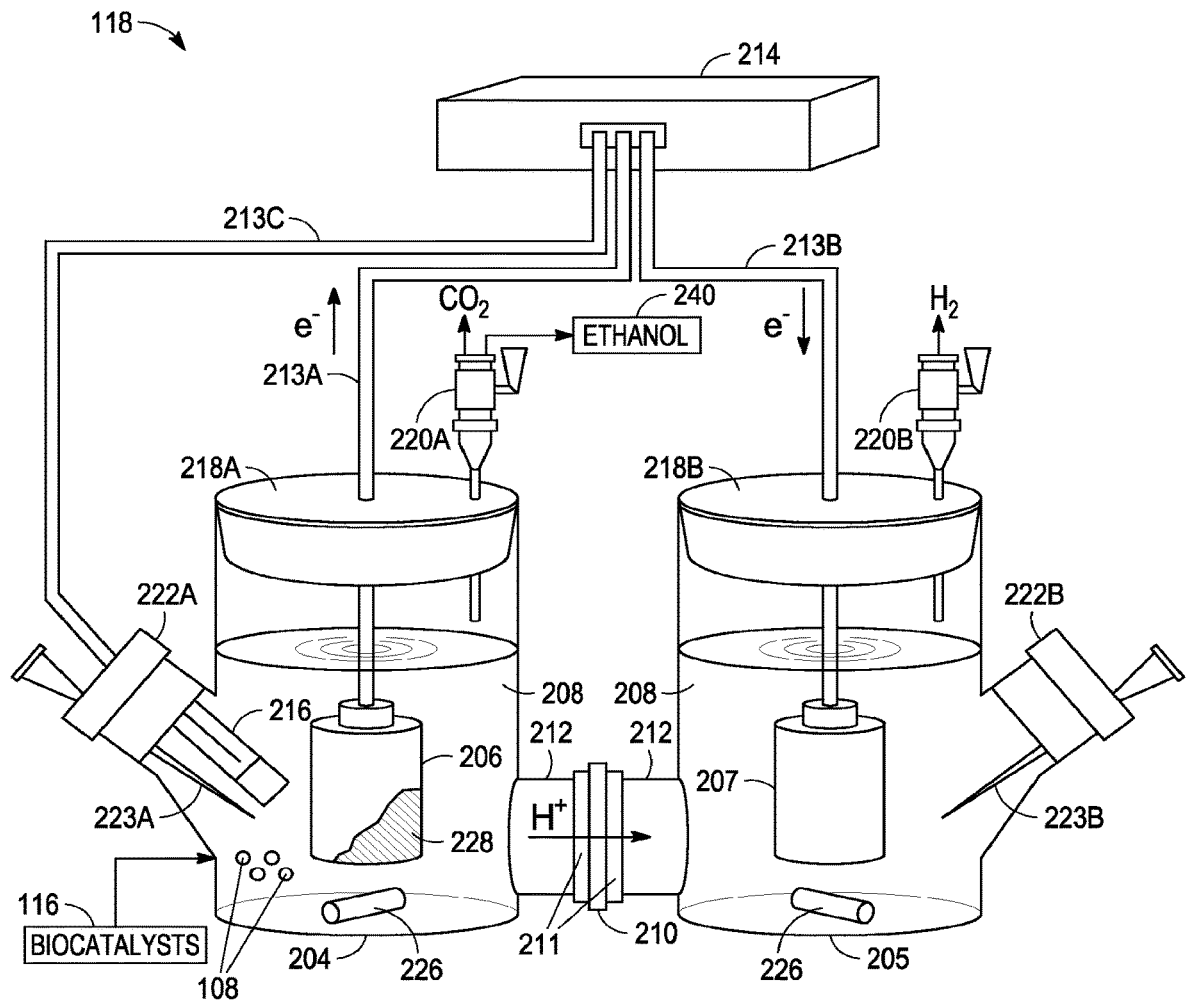
FIG. 2 is a simplified schematic of a microbial fuel cell (MFC) according to an embodiment.

In one embodiment, the electrode materials are selected from any known conductive material, including, but not limited to, carbon, precious or non-precious metals, metal-organic compounds, stainless steel, conductive polymers, and the like, further including combinations thereof. In one embodiment, the cathode electrode material and the anode electrode material are different materials. In one embodiment, each electrode can have any suitable configuration as is known to those skilled in the art, with each electrode having the same or a different configuration, as desired. In one embodiment, each electrode has a configuration selected from one or more sheets (made from any conductive material), or one or more of various types of cloth, paper, glass, brush and rods, and the like, or any combination thereof. Further details of one embodiment of a MFC are shown in FIG. 2.

In one embodiment, the CBP organism 110 not only hydrolyzes lignocellulosic substrates and produces ethanol at high yields (greater than 40% of maximum theoretical yield), but further primarily produces fermentation byproducts (including, for example, primarily organic acids and/or primarily hydrogen gas and/or primarily other fermentation byproducts known in the art), which are used as electron donors for growth of and electricity generation by an electricigen. In one embodiment, the CBP organism 110 is a microbe in the clostridial or cellulomonad groups. In one embodiment, Cellulomonas uda ATCC 21399 (hereinafter "Cuda" or "C. uda") is used, which produces primarily acetate and formate in addition to ethanol. The acetate and formate are converted into electricity by the electricigen Geobacter sulfurreducens (hereinafter "Gsu" or "G. sulfurreducens"). This process removes organic acids from the growth medium, which prevents media acidification and feedback inhibition of C. uda's fermentative metabolism. As a result, C. uda's growth and ethanol production are stimulated in the co-culture. Furthermore, because substantially all fermentation byproducts are converted into electricity, substantially all electrons potentially available for electricity generation are recovered and ethanol is the only fermentation product remaining in the liquid medium.

This is in contrast to certain known microbes, such as Clostridium cellulolyticum, which do not hydrolyze or ferment sufficiently, and also produce a wide range of fermentation byproducts, including those that cannot be converted into electricity by the electricigen. Such a platform leads to electron losses and accumulation of 'waste' fermentation byproducts, rather than net production of ethanol and electricity, as desired. As such, the embodiments described herein do not include use of Clostridium cellulolyticum as the CBP organism 110.

Any suitable electricigen 120 may be added to the anode chamber 202 to drive electricity generation. In one embodiment, the electricigen 120 produces conductive protein filaments termed "pilus nanowires" that allow substantial stacking of cells on the electrode and efficient electron flow across the electricigenic film and to the electrode. This includes, but is not limited to, members of the Geobacteraceae family, such as G. sulfurreducens.

In one embodiment, a cathodic chemical reaction, such as an oxygen or ferric cyanide oxidation reaction occurs in the cathode chamber. Such an embodiment may be used in applications where electronic input from a potentiostat is not feasible or cost-efficient.

Ethanol yields are expected to be higher than 30% of the total fermentation product. In one embodiment, the yield may be higher than 40%, 50%, 60%, 70%, 80%, 90% or higher, including any range there between.

This is in contrast to previous attempts by others to produce both ethanol and electricity (such as with C. cellulolyticum and partially amorphous cellulose, e.g., cellulose/hemicellulose, rather than insolubles 108), in which ethanol yields less than 40% are obtained, due to relatively inefficient conversion of fermentation byproducts into electricity. Such methods further require the electricigen to be previously grown in a separate microbial fuel cell. However, in an alternative embodiment, the electricigen (e.g., 120) and/or the CBP organism (e.g., 110), may optionally be grown in a separate microbial fuel cell although again, this is not required.

The novel systems and methods described herein are efficient, completing the one-step hydrolysis and fermentation process to produce a maximum ethanol yield with a desired CBP organism (e.g., 110) in a time period of less than about 50 hours. Generally, the time period is less than conventional methods of reaching a maximum ethanol yield through separate hydrolysis and fermentation steps, which can take more than 100 hrs, such as up to 120 hrs.

In one embodiment, ethanol yields of at least 80% of the maximum theoretical yield is produced after less than 50 hours, such as about 40 to 46 hours, approximately 43 hours and 80% of the maximum yields are produced after less than 50 hours, such as at least about 45 hours.

In the embodiment shown in FIG. 2, a MFC 118 is provided, which is an electrochemical cell comprising two chambers (i.e., anode chamber 204 and cathode chamber 205) in an "H" configuration. An anode electrode 206 is located in the anode chamber 204 and a cathode electrode 207 is located in the cathode chamber 205. A cation- or proton-exchange membrane 210, together with gaskets 211 and glass flanges 212, create a "glass bridge" which separates the anode and cathode chambers, 204 and 205, respectively.

In this embodiment, each chamber, 204 and 205 contains an amount of growth medium 208, which, in one embodiment, is substantially identical. The growth medium 208 can be any medium that supports growth of the biocatalysts 224, and do not necessarily need to be the same in each chamber, 204 and 205. In one embodiment, the growth medium 208 is fresh water (FW) (See Lovley, D. R., and E. J. P. Phillips. 1988. *Novel mode of microbial energy metabolism: organic carbon oxidation coupled to dissimilatory reduction of iron or manganese*. Appl Environ Microbiol. 54(6): 1472-1480), which is incorporated herein by reference in its entirety.

In one embodiment, the growth medium 208 further contains minerals, vitamins, or combinations thereof. In one embodiment, "Regan's medium" is used as the growth medium 208. (See Ren, Z., T. E. Ward, and J. M. Regan. 2007. *Electricity production from cellulose in a microbial fuel cell using a defined binary culture*. Environ. Sci. Technol. 41:4781-6, hereinafter "Regan") which is incorporated herein by reference in its entirety. In one embodiment, "Daniel Bond's medium" is used as the growth medium 208. (See Marsili, E., Rollefson, J. B., et al., 2008, *Microbial biofilm voltammetry: direct electrochemical characterization of catalytic electrode-attached biofilms*. Appl Environ Microbiol., December:74(23):7329-3), which is hereby incorporated herein by reference in its entirety. In one embodiment, the growth medium 208 is present in the anode chamber 204 and cathode chamber 205 in substantial quantities so all the electrodes are fully immersed.

The anode electrode 206 and the cathode electrode 207 are electronically connected via anode conductive wires and cathode conductive wires, 213A and 213B, respectively, both of which, in turn, are connected to a potentiostat 214. The anode chamber 204 further houses a reference electrode 216, which is also connected to the potentiostat 214 with conductive wires 213C, as shown in FIG. 2.

The anode chamber 204 and cathode chamber 205 are sealed with an anode stopper 218A and a cathode stopper 218B, respectively. An anode outlet port 220A is provided in the anode stopper 218A and a cathode outlet port 220B is provided in the cathode stopper 220B. The anode chamber 204 is further equipped with an anode sparging port 222A into which a first needle 223A can be inserted. Similarly, the cathode chamber 205 is equipped with a cathode sparging port 222B into which a second needle 223B can be inserted. The sparging ports, 222A and 222B, further include suitably sized stoppers, as is known in the art.

In use, the potentiostat 214 poises the anode electrode 206 at a defined potential, thus allowing for a cathode-unlimited system for controlled and reproducible results. In one embodiment, the process begins by adding a quantity of biomass insolubles 108 (e.g., pretreated corn stover) and a quantity of each biocatalyst 224 (i.e., one or more electricigens 120 and one or more CBP organisms 110, as shown in FIG. 1) to the anode chamber 204 to initiate biomass processing.

The insolubles 108 can have any suitable moisture content. In one embodiment, the moisture content is at least about 15%. The insolubles 108 may be dried prior to use, if, for example, they have been stored for a period of time, although such a step increases the cost of the process. Likewise, both biocatalysts 224 can take any form, including a solid or liquid. In one embodiment, at least one of the biocatalysts 224 is added as a substantially concentrated wet cell pellet. In one embodiment, it is added as a dry (lyophilized) powder.

The biocatalysts 224 can be added at substantially the same time or sequentially, as noted herein. As the single step hydrolysis and fermentation of the biomass insolubles 108 proceeds, ethanol 230 is produced in the anode chamber 204. In one embodiment, the ethanol 230 is gas-stripped from the growth medium 208 of the anode chamber 204 via the anode outlet port 220A and collected in another vessel or pipe as it is being produced, for immediate or for later distribution. In the embodiment shown in FIG. 2, ethanol 230 produced as a result of the fermentation is discharged through the anode outlet port 220A, although the invention is not so limited. Ethanol 230 can be drawn off in any suitable manner, including in a liquid phase.

In one embodiment, the anode outlet port 220A also allows carbon dioxide ($CO_2$) to be vented out of the MFC 118 during the fermentation portion of the single step hydrolysis and fermentation. In one embodiment, the $CO_2$ is collected and recycled for use in an off-site process.

Fermentation byproducts comprising primarily one or more organic acids (not shown) and an amount of hydrogen (Hf) produced with the single hydrolysis and fermentation step are exposed to a second biocatalyst 224 (i.e., electricigen 120, as shown in FIG. 1) causing an electricigenic film 228 to grow on the anode electrode 206. The electricigenic film 228 can grow to any suitable thickness. In one embodiment, the electricigenic film 228 is at least about 40 to about 50 micrometers thick.

The electricigenic film 228 catalyzes the split of electrons ($e^-$) and protons ($H^+$) present in the fermentation byproducts, causing the electrons ($e^-$) to flow from the anode electrode 206 towards the cathode electrode 207 (such as through conductive wires 213A, into the potentiostat 214, and into conductive wires 213B, as shown in FIG. 2). The protons ($H^+$) permeate the proton-exchange membrane 210 and react with the electrons ($e^-$) at the cathode electrode 207, thereby generating hydrogen gas ($H_2$). In the embodiment shown in FIG. 2, the hydrogen gas ($H_2$) generated in the cathode chamber 205 exits through the outlet port 220B.

Both sparging ports, 222A and 222B, are configured to remove oxygen gas, facilitate mixing, and/or provide defined gases for buffering the pH of the growth medium (e.g., $CO_2$-containing gas to buffer the pH of bicarbonate-containing medium) from their respective chambers, 204 and 205, and, ultimately from the MFC 118. Mixing also can be achieved with stir bars 224, as is known in the art.

In one embodiment, glycerol-containing water is used as feedstock to generate ethanol and/or electricity in a microbial electrochemical cell. The glycerin-containing water can be subjected to one or more pretreatment steps to remove unwanted components, such as oils and salts (while retaining both glycerol and, if present, alcohol). In one embodiment, the pretreatment additionally or alternatively includes a concentration step to increase concentration of the glycerol in the glycerin-containing wastewater to a desired level.

In this embodiment, therefore, the "insoluble" component (comparable to insolubles 108 in FIG. 1) is glycerin. As such the glycerin can be provided to a BEC, such as a MFC, (e.g., the MFC 118 shown in FIG. 1). The glycerin is then degraded, i.e., hydrolyzed and fermented in a single-step process using a consolidated bioprocessing (CBP) microbe (e.g., 110) to produce an alcohol (e.g., ethanol 112) and fermentation byproducts such as hydrogen gas ($H_2$) and organic acids. The hydrogen gas 114 and/or organic acids provide a source of electrons to support the growth of an electricigen as described in FIGS. 1 and 2. Again, as described herein with lignocellulosic biomass, glycerin-containing biomass embodiments described herein provide for use of a CBP organism which is not only capable of catalyzing the enzymatic hydrolysis, but can also serve as an alcohologenic biocatalyst (alcohologenesis). In one embodiment, the CBP organism 110 serves as an ethanologenic biocatalyst. (See further discussion above with respect to FIGS. 1 and 2, which is applicable to the glycerin embodiment).

Additionally, glycerol is a permeant solute which enters freely inside a cell, thus affecting the properties of the intracellular aqueous environment and enzymatic processes, which can lead to growth inhibition. Furthermore, the viscosity of the medium also increases at high glycerol loading and microbial cells can be osmotically stressed. In one embodiment glycerol tolerance of microbial catalysts useful as alcohologenic biocatalysts is increased by at least two fold up to about 10 fold. In one embodiment, the improvement is between about four and six fold. In one embodiment, the glycerol tolerance of microbial catalysts useful as alcohologenic biocatalysts is increased at least about 10-fold. (See also Example 5). With further modification of the microbial cells, it is possible the improvement may be even higher than 10-fold.

In one embodiment, the alcohologenic biocatalyst is *Clostridium cellobioparum* (Cce) which can ferment glycerol into ethanol and fermentation byproducts which can be converted into electricity with Gsu as the electricigen. In one embodiment, a glycerol-tolerant strain of Cce (CceA) or an alcohol-tolerant strain of Gsu (GsuA) or a co-culture of Cce-Gsu, CceA-GsuA or any combination thereof, including any combination with Cce, is used as the alcohologenic biocatalyst (See Example 5).

In one embodiment, allyl alcohol selection is used to further improve the performance of an alcohol-tolerant catalyst. In one embodiment, selective pressure on a glycerol tolerant catalyst, such as CceA, can be increased to accelerate the selection process by selecting for mutants in the ethanol dehydrogenase enzyme. This enzyme catalyzes the natural conversion of acetaldehyde to ethanol in clostridia but also converts allyl alcohol into acrolein. The presence of allyl alcohol in the growth medium is expected to rapidly select for variants that produce mutant ethanol dehydrogenase isoenzymes with diminished affinity for allyl alcohol while maintaining or increasing their affinity for acetaldehyde. As a result, these variants are expected to have high ethanol tolerance and high ethanologenic rates In one embodiment, this approach can be used to accelerate the selection for ethanol-tolerant strains of CceA with improved fermentative rates and higher ethanol yields. Variants have also been reported to arise that carry mutations that reduce the activity of the acetaldehyde dehydrogenase enzyme, which catalyzes the conversion of acetyl-CoA to acetaldehyde. However, these strains can be differentiated because they have not evolved alcohol tolerance and have reduced ethanol yields. Such variants can be prevented from growing by supplementing the growth medium with not only allyl alcohol, but ethanol. Thus, it is expected that the chances of isolating the desired variants can be increased by adding ethanol to the cultures as well.

Inasmuch as Gsu does not have the ethanol dehydrogenase enzyme, a different approach using elevated temperatures can be followed to increase the selective pressure for alcohol-tolerant strains of GsuA. In one embodiment, the incubation temperature of the chosen strain can be gradually increased from any suitable starting point lower than the optimal temperature for growth up to just above the optimal temperature for growth. In one embodiment, the incubation temperature can be gradually increased, starting at about 37° C. up to about 40° C. (e.g., 2° C. above the optimal temperature for growth of Gsu (an example electricigen) and Cce (an example CBP), respectively).

In one embodiment, growth can be monitored as optical density and cultures can also be transferred in stationary phase to capitalize on the error-prone behavior of DNA Polymerase IV. Growth rates are expected to decrease at first as suboptimal temperatures are used. However, maintaining the temperature selection is expected to eventually select for variants that have recovered the original growth rates. At this point, aliquots of the cultures can be preserved at a suitable temperature, such as down to about −80° C. The cultures can then be transferred and incubated at a higher temperature at the desired time. Eventually, it is expected that temperatures in which optimal growth rates do not recover can be reached, thus marking the end of the adaptive evolution. The heat-tolerant strains can then be tested for alcohol tolerance, which is expected to have increased at the ancestral growth temperature.

As described in the Examples below, the inventors are the first to provide a method for adaptively evolving glycerol tolerance in alcohologenic biocatalysts. In one embodiment using Cce as the biocatalyst, successive passages at increasing concentrations of glycerol can allow various strains to grow at high glycerol loads of up to about 10%, further up to about 20%. In one embodiment, CceA is grown at glycerol loads of up to about 10%.

In one embodiment, the ethanol tolerance of CceA is improved while simultaneously improving the glycerol tolerance, as the ethanol sensitivity of CceA can mask its true ability to grow and ferment higher loads of glycerol. In one embodiment, cells are grown with increasing concentrations of glycerol until their optical density stabilizes, which is a signal that the cells have entered a stationary phase of growth. At this phase, mutation rates are highest and the pressure to use glycerol selects for mutant variants with highest growth rates. In one embodiment, variants show improved growth, allowing them to outcompete the slower cells, and can be enriched in successive transfers. In one embodiment, positive selection of these variant proceeds, thus allowing the cultures to reach stationary phase faster.

Once the growth rates stabilize, in one embodiment, the cultures can again be transferred and allowed to grow to an early exponentially phase, where the most rapidly growing cells will predominate. In one embodiment, clonal variants can be isolated on glycerol-containing plates and grown in fresh liquid medium to an exponential phase. After successive transfers in exponential phase the fastest growers can be selected and preserved at a suitable temperature, such as a temperature down to about −80° C. In one embodiment, the variant with the highest growth rates and yields can be used to initiate a new round of adaptive evolution at the next glycerol increment.

In one embodiment alcohologenic biocatalysts in a co-culture are adaptively evolved to co-evolve traits of interest. In one embodiment, adaptively evolving a co-culture (i.e., more than one culture, such as CceA and GsuA), exerts a multiple selection on each component in the co-culture to tolerate higher glycerol loads, to ferment glycerol faster, to increase alcohol tolerance (as more alcohol accumulates), and to remove and utilize the fermentation byproducts (including lactate). Thus, a co-culture can be evolved to grow at increasing glycerol loadings. In one embodiment, a rapid fluorescence assay is used, which allows performance monitoring of a co-culture as a function of catalyst growth. In one embodiment, cell numbers of each of the strains in a co-culture are quantified by the assay by initially staining all cells in one color (e.g., green) with a suitable binding dye, such as a nucleic acid-binding dye SYTO 9 and counter-staining Gram-negative cells in another color (e.g., red) with a suitable acid-binding dye, such as fluorescent nucleic acid-binding dye hexidium iodide. See, for example, Haugland, R. P. *Molecular Probes. Handbook of fluorescent probes and research chemicals.*, (1999), which is incorporated herein by reference in its entirety.

The differential absorption and emission of the two dyes enables their rapid detection and quantification in a fluoro-plate reader. In one embodiment, dye intensity for the cell numbers of each strain in the co-culture is standardized and can measure the absolute cell number for each strain and the ratio of the two. The ratios are expected to be constant if no variants arise or if variants of the two arise simultaneously. Conversely, the ratios will likely change when variants of one or the other arise first. Growth can be routinely monitored as optical density. Those co-cultures showing improved growth rates can be analyzed with the fluorescence assay described above to quantify the catalysts' growth and calculate the ratios.

In one embodiment, the co-cultures follow a step-wise evolution since the chances of one positive variant arising in only one member are higher than the probability of positive and complementary mutations arising in the two microbial catalysts simultaneously. For example, CceA variants with increased fermentation rates may arise first, which can produce more fermentation products. This can add selective pressure on GsuA to tolerate higher concentrations of growth inhibitors (e.g., ethanol or lactate) and remove electron donors faster. Thus, GsuA variants with enhanced tolerance, uptake and/or metabolism of fermentation products can be selected for in successive transfers. This can result in increased cell numbers for GsuA and recovery of the ratios of the two microbial catalysts. In one embodiment, when variants arise, aliquots are plated in solid medium supplemented with a suitable amount of glucose, acetate and/or fumarate to isolate individual quantities, i.e., an amount sufficient to support enough doubling times from a single cell so the colony is visible to the naked eye. In one embodiment, about 0.2% (w/v) glucose is used for CceA and about 0.2% (w/v) acetate and fumarate is used for GsuA. Thereafter, clonal selection, growth, storage, and tests for alcohol and glycerol tolerance and fermentation can be performed as described in the example section.

In one embodiment, genetic engineering is used to improve performance of the alcohologenic biocatalyst. Although adaptive evolution can be used to improve the electrical conversion of lactate by Gsu, the availability of a genetic system for this organism enables the application of genetic engineering tools as well. The genetic basis of Gsu's inefficient lactate utilization has been well studied. Strains of Gsu adaptively evolved to grow in lactate media with doubling times comparable to the preferred electron donor, acetate, have been isolated and their genome, sequenced. Summers, Z. M. et al. in *Genomics: GTL Contractor-Grantee Workshop VII*, (ed. Office of Science U.S. Department of Energy) 121 (Genome Management Information System (Oak Ridge National Laboratory)), which is incorporated herein by reference in its entirety. All of the lactate-adapted strains had single base-pair substitutions in a gene (GSU0514) encoding a repressor of the succinyl-CoA synthetase enzyme. This enzyme catalyzes the conversion of succinyl-CoA to succinate in the TCA cycle when acetate is not the electron donor. Because the GSU0514 repressor also regulates the activity of other genes, it is important to select for single point mutations that activate the succinyl-CoA synthetase gene without disrupting the normal functioning of the cell. In one embodiment, random mutagenesis can be performed by rolling circle error prone PCR, a method in which the PCR-amplified GSU0514 is first cloned into the GsuA expression vector pRG5 and then amplified in its entirety under error-prone conditions to introduce random mutations. See, for example, Fujii, R., Kitaoka, M. & Hayashi, K. One-step random mutagenesis by error-prone rolling circle amplification. Nucleic Acids Res. 32, e145, doi:32/19/e145 [pii] 10.1093/nar/gnh147 (2004) and Coppi, M. V., Leang, C., Sandler, S. J. & Lovley, D. R. Development of a genetic system for *Geobacter sulfurreducens*. Appl. Environ. Microbiol. 67, 3180-3187 (2001) (hereinafter "Coppi"), both of which are incorporated by reference in their entireties.

In one embodiment, the plasmid mix can then be electroporated in a GSU0514-deletion mutant of GsuA using recombinant PCR techniques and mutants of interest can be isolated based on their ability to grow on solid medium with lactate as sole electron donor. (See Coppi). In one embodiment, the mutants with the fastest growth rates can be introduced into GsuA via recombinant PCR to generate stable mutants, which can then be tested in a BEC powered with lactate as an electron donor (See Coppi).

In one embodiment, the "H" configuration MFC (shown in FIG. 2) with the anode electrode poised to a fixed potential is used. In one embodiment, lactate removal from the medium can be monitored by HPLC using a UV detector. The electrical conversion of lactate can then be calculated as coulombic efficiency (the amount of usable electrons in the lactate consumed (12 electrons per mol) divided by the electrons measured as current). In one embodiment, coulombic efficiencies similar to the preferred electron donor, acetate, (such as about 80% up to about 90%), are reached.

In one embodiment, a mutant of CceA defective in lactate production is genetically engineered. The mutation can be introduced into a selected adaptively evolved strain, such as one showing high alcohol tolerance, glycerol loading, and growth robustness. *Clostridia* are known to produce lactate in a single reaction from pyruvate that is catalyzed by the lactate dehydrogenase enzyme. See, for example, Yazdani, S S., et al, Anaerobic fermentation of glycerol: a path to economic viability for the biofuels industry, Current Opinion in Biotechnology, Volume 18, Issue 3, June 2007, Pages 213-219, which is incorporated herein by reference in its entirety. Although the genome sequence of Cce is not available, many other closely-related, clostridial genomes are. See, for example, Collins, M. D. et al. The phylogeny of the genus *Clostridium*: proposal of five new genera and eleven new species combinations. *Int. J. Syst. Bacteriol.* 44, 812-826 (1994), which is incorporated herein by reference in its entirety.

In one embodiment, the high conservation of clostridial lactate dehydrogenase genes can allow alignment of the sequences and identification of regions of conservation for the design of degenerate PCR primers. These primers can be used to amplify the Cce lactate dehydrogenase gene, which will be sequenced. A universal genetic system is available for targeted mutagenesis in clostridia, which allows for the generation of stable insertion mutants in just a few (10 to 14) days. See, for example, Heap, J. T., Pennington, O. J., Cartman, S. T., Carter, G. P. & Minton, N. P. The ClosTron: a universal gene knock-out system for the genus *Clostridium*. *J. Microbiol. Methods* 70, 452-464, doi:S0167-7012(07)00208-4 [pii] 10.1016/j.mimet.2007.05.021 (2007) (hereinafter "Heap 2007") and Heap, J. T. et al. The ClosTron: Mutagenesis in *Clostridium* refined and streamlined. *J. Microbiol. Methods* 80, 49-55, doi:50167-7012(09) 00350-9 [pii] 10.1016/j.mimet.2009.10.018 (2010) (hereinafter "Heap 2010"), both of which are herein incorporated by reference in their entireties. The method, known as the ClosTron, consists of a plasmid with a bacterial group II intron sequence where a short sequence of the targeted gene is cloned. The plasmid is introduced in the bacterium by electroporation and positive clones are selected in the presence of the plasmid's antibiotic. See, for example, Phillips-Jones, M. K. in *Electroporation protocols for microorganisms* Vol. 47 (ed J. A. Nickoloff) Ch. 23, 227-235 (Humana Press Inc., 1995), which is incorporated herein by reference in its entirety. In one embodiment, the CceA minimum inhibitory concentration to the antibiotics available in the various ClosTron plasmids is established (See Heap 2007 and Heap 2010). In one embodiment, the specific ClosTron target is synthesized for the lactate dehydrogenase. The plasmid replicates in the clostridial host and constitutively expresses the intron, which spontaneously inserts itself into the chromosome at the targeted location. The clones with an intron insertion become resistant to a second antibiotic and can be easily isolated on selective plates. The plasmid is later lost producing a stable insertion in the gene of choice. In one embodiment, the lactate mutant of CceA can be grown with glycerol to confirm it does not produce lactate. Because more pyruvate is available for acetate and ethanol production, higher current (from acetate) and/or ethanol yields are expected.

Ethanol production in clostridia proceeds in two reactions catalyzed by the acetaldehyde and ethanol dehydrogenase enzymes. In one embodiment, an ethanol-deficient mutant of Cce may be produced. In one embodiment, genetic engineering is used to inactivate the first reaction to effectively reroute the acetyl-CoA towards the synthesis of acetate. The acetyl-CoA to acetate reaction generates ATP and is expected to be energetically favored. The result is an ethanol-deficient mutant that predominantly ferments glycerol to acetate. In one embodiment, the mutation can be introduced in a lactate-deficient CceA strain to generate a mutant that ferments glycerol to acetate, formate and $H_2$ only. Because these are the electron donors that have the highest electrical conversion rates by Gsu, current production in a MFC is expected to increase.

Electrochemical parameters can be further improved to increase the efficiency of the platform in the MFC. In one embodiment, the voltage potential of the MFC, for example, can be adjusted to promote efficient electrical conversion of the fermentation byproduct mix.

In one embodiment, the power density obtainable with the glycerol embodiment is improved as compared to conventional microbial fuel cells. In one embodiment, the efficiency of glycerol removal is also improved as compared to conventional microbial fuel cells. In one embodiment, the columbic efficiency of the glycerol embodiment is also improved as compared to conventional microbial cells. In one embodiment, the concentration of glycerol used is greater than 2.5% by volume, such as up to about 10% or higher, up to about 20%, about 30%, about 40%, about 50%, about 60%, about 70%, about 80%, about 90%, up to substantially pure glycerol, including any ranges there between. In one embodiment, the concentration of glycerol in the glycerin-containing water is at least about 50% up to about 80%. In one embodiment, the electrogenic activity is improved as compared to a conventional microbial fuel cell. In one embodiment, the electrogenic activity does not require the addition of a redox mediator as compared to a conventional microbial fuel cell. In one embodiment, the alcohologenic biocatalyst is not an "opportunistic" pathogen as that term is understood in the art.

In one embodiment, the processes described above are scalable up 10, 100 to 1000 times or more for large-scale ethanol and electricity production. In one embodiment, the electricity generated can be used to replace some of the electricity demand of a biofuel production facility, such as an ethanol and/or biodiesel production facility. In one embodiment, electricity is produced using a bioelectrochemical cell (BEC). In one embodiment, the ethanol produced according to the methods described herein can be distilled in a biodiesel production facility using existing distillation equipment and reused as the alcohol in the transesterification reaction.

Embodiments described herein include computer-implemented systems and methods operating according to particular functions or algorithms which may be implemented in software or a combination of software and human implemented procedures. In one embodiment, the software may comprise computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer, i.e., a computer system, such as a personal computer, server or other computer system.

Embodiments of the invention will be further described by reference to the following examples, which are offered to further illustrate various embodiments of the present invention. It should be understood, however, that many variations and modifications may be made while remaining within the scope of the present invention.

Example 1

Preliminary experiments were performed to select a CBP organism and to show that byproducts of ethanol fermentation produced by a CBP organism from lignocellulosic substrates can be converted into $CO_2$ and electrons by an electricigen. In these experiments, the lignocellulosic substrate was AFEX-treated corn stover (hereinafter termed AFEX-CS), the CBP organism was *C. uda* and the electricigen used was *G. sulfurreducens* (Gsu) which catalyzed the conversion of fermentation byproducts using a chemical electron acceptor (fumarate). These experiments also demonstrated that rates of ethanol production were increased by at least ten (10)% up to about 15% during co-culture growth through the removal of fermentation byproducts whose accumulation would otherwise inhibit the consolidated bioprocessing step and/or ethanologenesis.

Equipment

Liquid fermentation byproducts such as ethanol and organic acids in supernatant fluids were analyzed by in a High Performance Liquid Chromatography (HPLC) system equipped with a 25P pump running at 0.6 mL/min and ~1600 PSI, in-line degasser AF, 2487 dual wavelength absorbance detector, 410 Differential refractometer, and 717Plus autosampler (Waters, Milford, Mass.) and a standard Cartridge Holder #125-0131 with a 30×4.6 mm Micro-Guard Carbo-C Refill Cartridge connected to an Aminex HPX-87H Ion exclusion column (Bio-Rad). The column was heated at temperature 25° C. Approximately 100 µl of sample was injected for analyses and metabolite separation was achieved using in a carrier solution of 4 mM $H_2SO_4$ in dd$H_2O$. Data acquisition was with a Microsoft Compaq computer equipped with Breeze software (Waters, Milford, Mass.). Gaseous fermentation byproducts such as $H_2$ and $CO_2$ were analyzed in a CP-4900 Micro Gas Chromatograph (Varian, Inc, Palo Alto, Calif.) equipped with a MSAH BF column with >99.999% Argon carrier gas and a PPQ column with >99.99% Helium carrier gas. Data collection was with a Dell Latitude D620 computer running Galaxie Chromatography Data System version 1.9.3.2 (Varian, Inc, Palo Alto, Calif.).

Starting Materials

Chemicals

All chemicals were from Sigma-Aldrich and had a minimum purity of 98%. For Gsu growth, sodium acetate and sodium fumarate were routinely used as electron donor and acceptor, respectively. CBP organisms were routinely grown with sugars such as cellobiose, glucose and xylose.

Substrate

Ammonia Fiber Expansion ("AFEX") treated corn stover (everything remaining after grain is harvested, typically including stalks and leaves w/o cobs) was used as the substrate in this testing. AFEX-CS was provided from Dr. Dale's Laboratory, Michigan State University (East Lansing, Mich.). It was prepared from corn stover (CS), premilled and passed through a 4 mm screen, provided by the National Renewable Energy Laboratory (NREL, Golden, Colo.). The moisture content of the untreated CS was about 7% (total weight basis). Feedstock analysis by NREL revealed an estimated composition (dry weight basis) of 34.1% cellulose, 22.8% xylan, 4.2% arabinan, 11.4% lignin and 2.3% protein in the corn stover. The milled CS was kept at 4° C. for long-term storage. The AFEX pretreatment was conducted in a 2.0 L pressure vessel (Parr) equipped with thermocouples and a pressure sensor. The vessel was heated to 100 to 110° C. before 240 g of prewetted CS at 60% moisture (dry weight basis) was loaded. The lid was bolted shut. Concurrently, 150 g anhydrous ammonia was added to a separate 500 ml stainless steel cylinder (Parker Instrumentation) and heated until the gas pressure reached 4.48 MPa (650 psi). Heated ammonia was then transferred into the reactor to initiate the reaction. After 15 min, the pressure was released through an exhaust valve. The initial and final temperatures of the pretreatment were 130±5° C. and 110±5° C., respectively. After AFEX treatment, pretreated CS was air-dried overnight under a fume hood, and kept at 4° C. for long-term storage. Approximately 125 g of AFEX-CS were supplied to this laboratory in a one-gallon ZIPLOCK bag and stored at four (4) ° C. The AFEX-CS was ground in a grinder (GE Model 168940) and sieved through a ceramic filter with 0.75 mm×0.75 mm pores.

Consolidated Bioprocessing (CPB) Organisms

*Clostridium cellulolyticum*, *Clostridium hungatei* AD, *Clostridium hungatei* B3B, *Clostridium papyrosolvens* C7, *Ruminococcus albus*, *C. uda* ATCC 21399, *Cellulomonas biazotea*, *Cellulomonas cartae*, *Cellulomonas gelida*, *Cellulomonas fimi*, *Cellulomonas uda* ATCC 491, *Cellulomonas flavigena*, *Clostridium cellobioparum*, *Clostridium longisporum*, *Clostridium populeti*, *Clostridium cellulovorans*, *Clostridium phytofermentans*, *Clostridium lentocellum*, *C. papyrosolvens* NCIMB from the inventors' laboratory culture collection were used.

These strains originated from a laboratory culture collection at the University of Massachusetts (Amherst, Mass.). The strains were grown in GS2 medium, as described in "Cellulase system of a free-living, mesophilic clostridium (strain C7)" K Cavedon, S B Leschine and E Canale-Parola J Bacteriol. 1990 August; 172(8): 4222-4230, which is incorporated herein by reference in its entirety, with 0.2% cellobiose or 0.2% glucose as the sole carbon and energy source. The strains were incubated at 30° C. Frozen stocks in 10% dimethyl sulfoxide were maintained at −80° C. for long-term storage.

*Acetivibrio cellulolyticus* ATCC 33288 (Ace) was purchased from The American Type Culture Collection ATCC (Manassas, Va.) for use in these preliminary experiments. It was cultured in a medium known as ATCC 1207 (ATCC, Manassas, Va.) and incubated at 37° C.

Electricigen

*G. sulfurreducens* ATCC 51573 (Gsu) was used as the electricigen. This microbe was obtained originally from the American Type Culture Collection (ATCC) as a substantially pure culture and maintained under conditions known in the art in the inventors' laboratory culture collection.

Procedure

The various organisms were screened for ethanologenic efficiency in "Regan's medium," see Regan, supra. AFEX-CS (0.2%) was added as source of carbon and energy. Fermentation efficiencies were assessed by first quantifying the ethanol yields and then the yields of liquid (organic acids) and gaseous (hydrogen and $CO_2$) fermentation byproducts in one to two week cultures via HPLC or GC analyses.

For co-culture experiments between Cuda and Gsu, strains were pre-grown to mid to late exponential phase in Regan's medium with, respectively, 0.2% D+ cellobiose or 15 mM acetate and 40 mM fumarate and incubated at 30° C. in a rotating drum incubator (Glas-Col 099A RD4512) run at low speed (10 percent). Approximately a 10% (v/v) inoculum with an optical density at 660 nm of 0.2 was added to anaerobic ($N_2$:$CO_2$. 80:20) pressure tubes (Bellco) containing 10 ml of Regan's medium and 0.2% AFEX-CS. Controls with Cuda alone (with or without 40 mM fumarate), Gsu alone, and uninoculated controls also were included. All cultures tubes were incubated at 30° C. in a rotating drum incubator, as described above.

Growth was monitored periodically by taking the optical density of the cultures at 660 nm. For growth measurements, the tubes were removed from the rotating incubator and the AFEX-CS was allowed to settle to the bottom of the tube for ~10 minutes prior to measuring the optical density of the culture. The uninoculated control tubes were used to calibrate the absorbance readings to zero.

The headspace of each tube was sampled periodically (every 1-3 days) to analyze the gas composition (hydrogen and $CO_2$) by gas chromatography (GC). Approximately 1 mL of headspace was removed with a $N_2$-flushed syringe and injected into the GC. Supernatant samples (0.7 ml) were also removed anaerobically, 70 μl were used to plate on solid Regan's medium supplemented with 0.2% cellobiose and measure growth of Cuda as colony forming units. The rest of the sample was filtered through a 0.45 μM membrane filter (Fisher) and stored at −20° C. before being analyzed by HPLC.

Initial Screening and Results

After one-to-two weeks of incubation at 30° C. the ethanologenic efficiency of each organism was assessed by measuring the yields of ethanol in cell-free supernatant fluids. The best ethanologens (ethanol yields more than 40% of the maximum theoretical yields) were *C. populeti*, *C. lentocellum*, *A. cellulolyticus*, *C. gelida*, *C. biazotea*, and *C. uda* ATCC 21399. The other strains were discarded.

Further Screening and Results

The liquid (organic acids) and gaseous (hydrogen gas and CO2) fermentation byproducts from the selected ethanologenic strains were measured by HPLC and GC analyses, respectively. Based on the predominant fermentation byproduct (hydrogen or organic acids) the strains in this testing were two functional categories.

The first group (*C. populeti*, *C. lentocellum*, and *A. cellulolyticus*) produced $H_2$ as their main fermentation product.

*C. populeti* was discarded because growth studies using soluble sugars such as 0.2% glucose revealed abrupt cell lysis as the culture reached cell densities more than 0.6 units of absorbance at 600 nm, which is consistent with the presence of lytic phage infection in this organism. Lytic phage infections have been reported in the genus *Clostridium* and are a major source of contamination in industrial fermentations. Infected strains are difficult to cure of the virus and are not desirable for industrial processes.

Figure 3:
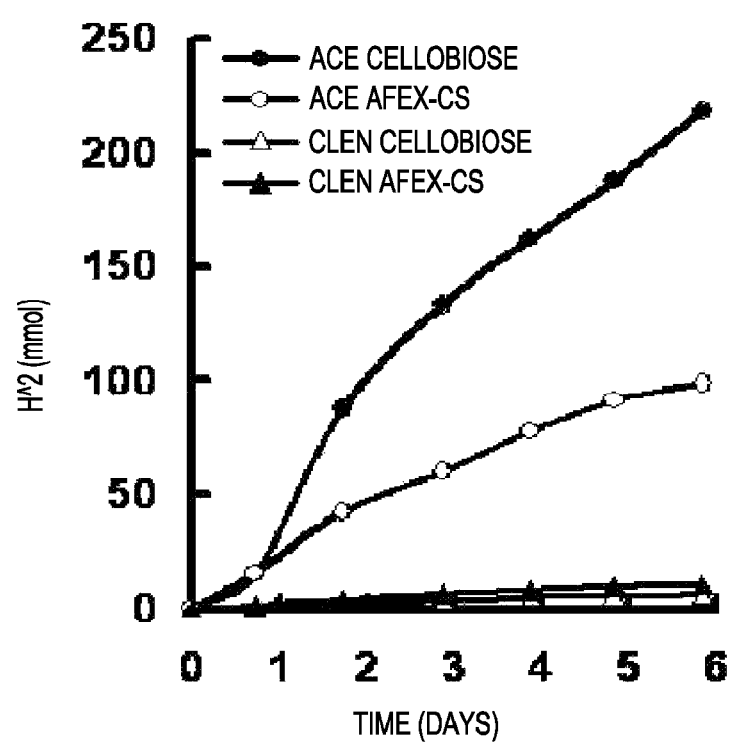
FIG. 3 shows hydrogen ($H_2$) production versus time for cellobiose and Ammonia Fiber Expansion (AFEX)-corn stover (CS) with *Acetivibrio celluloyticus* (Ace) or *Clostridium lentocellum* (Clen) as the consolidated bioprocessing (CBP) organisms according to various embodiments.

Otherwise, as FIG. 3 shows, Ace produced significantly more $H_2$ than *C. lentocellum* during the degradation of AFEX-CS and during the fermentation of the cellulose repeating disaccharide unit, cellobiose. Acetate and formate were the predominant organic acids produced during fermentation of AFEX-CS by both Ace and Clen (not shown).

The second group (*C. gelida*, *C. biazotea*, and *C. uda* ATCC 21399) consisted of members of the family Cellulomonadaceae, a group of facultative aerobic actinobacteria, and produced predominantly organic acids (mainly acetate and/or formate) as fermentation products, with very little or undetectable fermentative hydrogen gas.

The high level of organic acid production by the organisms in this group led to media acidification during fermentation, thereby causing suboptimal growth and fermentation. In the case of *C. uda*, the pH of the medium dropped from 7 to 5.5 during the degradation and fermentation of AFEX-CS, Thus, removal of organic acids is expected to have a positive effect in cell growth and ethanologenesis.

Figure 4:
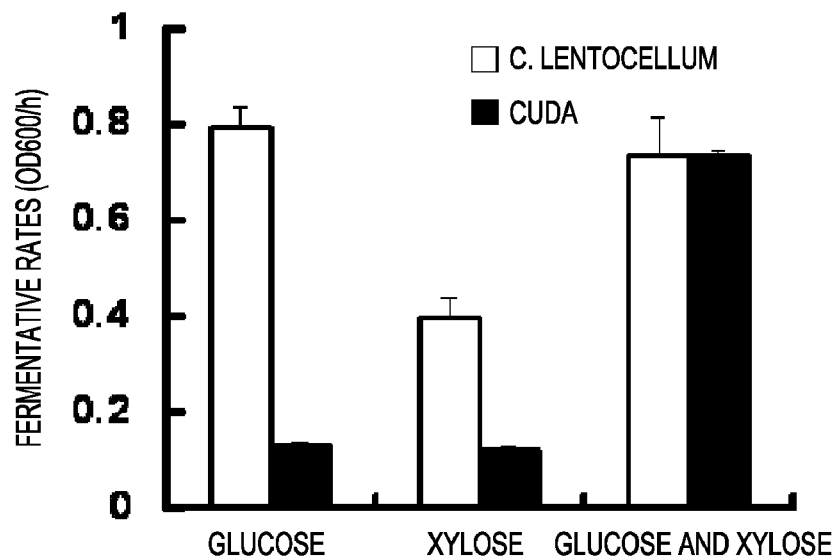
FIG. 4 is a bar graph showing fermentative growth rates of Clen and *Cellulomonas uda* ATCC 21399 (Cuda) with glucose, xylose, or both, according to various embodiments.

As compared with Cuda, *C. lentocellum* had a higher growth rate during the co-fermentation of glucose and xylose, as shown in FIG. 4.

Specifically, the growth rates for the fermentation of single sugars was six- and three-fold higher for *C. lentocellum* as compared with Cuda when grown, with 0.2% glucose and 0.2% xylose, respectively, which makes *C. lentocellum* a more robust strain for industrial fermentations of the individual sugars.

However, the co-fermentation rates of Cuda and Clen were comparable, as shown in FIG. 4, which makes them attractive candidates for fermentations based on lignocellulose substrates.

In addition, Cuda was the only cellulomonad that grew optimally under the anaerobic conditions useful for optimum fuel cell performance. Cuda also produced the highest yields of acetate and formate, namely more than 20 mM and 30 mM, respectively. For this reason, it was selected for further studies.

Testing Fermentation Byproducts Removal by Gsu

Based on the above results, removal of organic acids to support growth of Gsu was predicted to prevent media acidification in cultures of Cuda grown with AFEX-CS and therefore increase cell viability and ethanol yields. To test this hypothesis, Cuda with Gsu were co-cultivated in culture vessels with AFEX-CS as sole source of carbon and energy, with fumarate as an electron acceptor for growth of Gsu. Negative controls with Gsu alone (which could not grow with AFEX-CS as an electron donor and fumarate as an electron acceptor) and in co-culture with Cuda but in media without fumarate (which serves as electron acceptor for growth of Gsu) were used to demonstrate that any metabolic changes were a consequence of consortium synthrophic growth.

Figure 5:
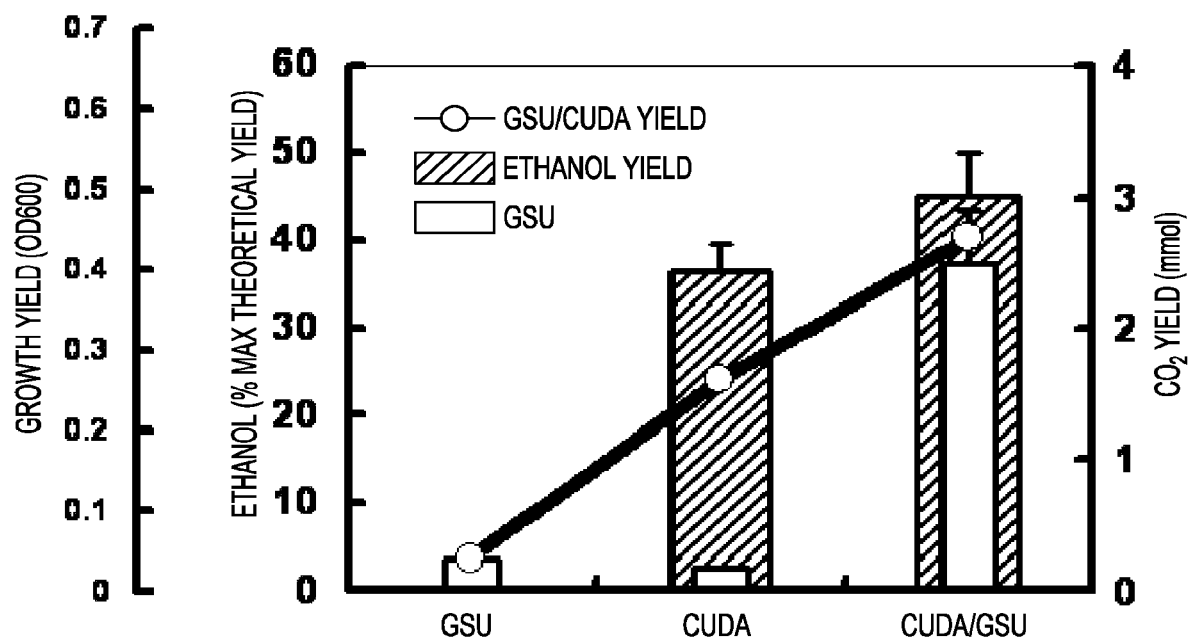
FIG. 5 is a bar graph showing ethanol yields and carbon dioxide ($CO_2$) yields using AFEX-CS with *Geobacter sulfurreducens* ATCC 51573 (Gsu) and Cuda alone, and in co-culture, in various embodiments.

As FIG. 5 shows, when grown in co-culture, the rates of biomass degradation by Cuda increased approximately 10 to 15%, as did the ethanol yields of Gsu. The growth of Cuda also was stimulated more than 15-fold as fermentation byproducts were removed by Gsu, as measured by the increase in Cuda's colony forming units. The growth of both Cuda and Gsu also is shown as absorbance at 660 nm in FIG. 5. In addition, all fermentation byproducts (organic acids and hydrogen) were used by Gsu, in a process coupled to the reduction of fumarate in the medium, which was monitored by the accumulation of succinate. $CO_2$ produced from the complete oxidation of acetate was used as a proxy for Gsu growth, which increased during co-cultivation of the two strains.

Conclusion

These results demonstrate that coupling an appropriate CBP organism to an electricigen works effectively to remove fermentation byproducts and increase the rates of biomass degradation and bioethanol production. These results further demonstrated that removal of organic acids effectively increased growth of Cuda. However, the amount of ethanol did not increase linearly.

Of all the organisms tested, *C. populeti, C. lentocellum, A. cellulolyticus, C. gelida, C. biazotea,* and *C. uda* ATCC 21399 were among the best ethanologens.

Cuda, along with the clostridial strain *C. lentocellum* described above, had the highest ethanol yields from AFEX-CS.

Cuda and *C. lentocellum* also had the highest growth rates during the anaerobic co-fermentation of six- and five-carbon sugars.

Co-culturing of Cuda with Gsu stimulated the growth of the CBP organism with AFEX-CS and the yields of ethanol while supporting the removal of fermentation byproducts and electron transfer by Gsu.

Example 2

Optimization of a MFC

A Precision Mechanical Convection incubator (cat no. 51220098) was customized to house electronic equipment and electrical cords connecting a customized MFC described below to an external potentiostat (Bio-Logic USA, VSP model) and connected to a Dell Inspiron 1721 laptop computer running the EC-Lab software V9.55 (Bio-Logic USA), which controlled the electrochemical parameters of the MFC and stored the output data.

An H-type, two-chambered microbial fuel cell was built and tested as shown in FIG. 2 and described above. The chamber volumes (100 ml) were reduced by 5-times the volume of standard H-type fuel cells (as described in *Improved fuel cell and electrode designs for producing electricity from microbial degradation*, Park D H, Zeikus J G. Biotechnol Bioeng. 2003 Feb. 5; 81(3):348-55), which is incorporated herein by reference in its entirety, to minimize the costs associated with each run, maintain anaerobiosis and improve reproducibility. The fuel cells were also designed such that both the anode and cathode of four (4) fuel cells could be stirred with a single 10-place stir plate (Fisher Scientific, IKAMAG) enabling four experiments to be carried out simultaneously.

Several anode and cathode electrode configurations were tested. A platinum wire can be used as the cathode electrode, however cheaper graphite materials were tested in order to minimize costs and increase electrode surface area. The electrode materials tested were graphite with different degrees of porosity (i.e., fine woven graphite felt (Electrosynthesis), porous graphite blocks, and graphite cylinders (>99% purity, Alfa Aesar), which were tested to find the most inexpensive material that could produce reproducible results and be reusable. The graphite cylinders had the lowest resistance of the electrode materials (i.e. less than 0.5Ω) and were the most durable so they were used for the anode and cathode electrodes.

Three types of connectors were tested for use with the graphite cylinders: 0.5 mm platinum wire (Electrosynthesis), 0.5 mm copper wire, and commercially available water-tight glass-reinforced epoxy connectors (Teledyne Impulse, XSA-BC) which connect to an approximately two (2) ft stranded wire (Teledyne Impulse, RMA-FS). Conductive silver epoxy (Fulton Radio, Inc.) was used to seal the connections. The commercially available connectors performed the best because they were inexpensive, created a tight seal to protect the wire and silver epoxy connections from corrosion, were the most durable, and allowed the electrodes to be removed from the fuel cell for further analysis (e.g. confocal microscopy). The completed electrodes had resistances of less than 0.5Ω.

Three different types of growth media were tested in the optimized fuel cell configuration, namely fresh water (FW), Regan media and Daniel Bond media ("DB"). All growth media were supplemented with 1-15 mM acetate. No current was produced when the Gsu culture was initiated in Regan media. Current was produced from FW and DB, however the conversion efficiency in DB was greater than 70% while the conversion for FW was ~20%. Additionally, DB media supported the growth of Gsu as well as many of the tested CBP organisms, including Cuda, and so was chosen as the preferred fuel cell media.

Gsu cell inoculation conditions were also optimized. The cells were grown in FW+ Ferric citrate media supplemented with 15 mM acetate (See *Development of a Genetic System for Geobacter sulfurreducens*. Coppi M V, Leang C, Sandler S J, and Lovley D R. Applied and Environmental Microbiology. 2001 July; Vol. 67(7): 3180-3187, which is incorporated herein by reference in its entirety), FW media supplemented with 15 mM acetate and 40 mM fumarate and DB media supplemented with 15-20 mM acetate and 40 mM fumarate.

The 40% vol/vol of cells (i.e. 36 mL) were harvested at late exponential phase, centrifuged to remove the excess acetate and fumarate, washed and then resuspended in fuel cell media and inoculated into the anode chamber. The cells from the DB media started producing current after approximately 18 hours while the cells from FW took approximately 24 hours, and the cells from FW+ ferric citrate took approximately 5 hours but did not proceed into exponential growth phase until approximately 48 hours. DB media was therefore chosen as the inoculation media for the Gsu cells because they performed well and because it is convenient to use the same media for all stages of the fuel cell setup.

Inoculation conditions were further optimized by testing the current production rates from cells grown to exponential phase and those grown to early stationary phase. Cells inoculated from stationary phase start producing current sooner (at approximately 12 hrs) so this inoculation condition was chosen.

Details of the optimized double chamber MFC are in Example 3 below.

Example 3

Unless otherwise indicated, all materials (including AFEX-CS) used were as described in Examples 1 and 2 above.

Microbial Fuel Cell (MFC)

The MFC optimized as described above in Example 2, was constructed and used in this testing. For convenience, reference numbers are directed to the exemplary MFC 118 shown in FIG. 2, although FIG. 2 is not to be interpreted as limited to the specific sizes, materials and configurations of the components described in this example.

The anode and cathode chambers (e.g., 204 and 205), respectively, were constructed from 100-mL Pyrex media bottles (Fisher Scientific). Custom-made glass side ports were fused to the bottles (Michigan State University glass shop) using 18-mm diameter glass pressure tubes (Bellco). The various ports (e.g., 220A, 220B, 222A and 222B) were sealed with 18-mm septum stoppers (Fisher Scientific).

The electrodes (e.g., 206 and 207) used in the MFC were 2.5 cm-long graphite rods, each having removable water-sealed connectors, to allow for removal of the wires from the electrode when needed, for example, to examine the microbial biofilm formed on the electrode by microscopy or to clean them after each use.

A glass bridge (comprising, for example, the cation exchange membrane 210, gaskets 211 and glass flanges 212) was constructed with a 15-mm diameter glass tube and a 32-mm diameter glass flange. A 32-mm diameter NAFION cation exchange membrane (Ion Power, Inc. N117) was sandwiched between two 32-mm diameter rubber gaskets (purchased at a local hardware store and modified to have a 15-mm hole in the middle). The glass flanges allowed for passage of H+ ions, but also served to keep the contents of each chamber separated. The NAFION membrane was cut into small circles, sandwiched between the rubber gaskets and sealed with epoxy between the two chambers. The NAFION membrane, rubber gaskets and glass flanges assembly were held together with a metal joint pinch clamp (Thomas Scientific).

The anode and cathode electrodes were constructed from 2.5 cm×1.3 cm graphite rods (Alfa Aesar), which were drilled to house a glass-reinforced epoxy connector (Teledyne Impulse, XSA-BC). Silver epoxy (Fulton Radio, Inc.) was used to make a tight conductive seal between the graphite and the connector such that the electrodes had less than 0.5Ω resistance. The imbedded connector was connected via a water-tight seal to a rubber-molded connector with an approximately two (2) ft stranded wire (Teledyne Impulse, RMA-FS).

The anode and cathode wires were imbedded into a No. 6 rubber stopper at the mouth of each chamber. Between experiments, the graphite electrodes were refreshed by soaking briefly in 1N HCl to remove trace metals, and 1N NaOH to remove organic material. The graphite was then polished with 400 grit sandpaper and rinsed in double distilled $H_2O$.

An Ag/AgCl reference electrode (Bioanalytical systems, Inc. MF-2078) was placed in the anode chamber using the sparging port (e.g., 222A). This enabled the potential of the anode electrode (e.g., 206) to be controlled using the potentiostat (Bio-Logic USA, VSP model). The cable of the reference electrode (e.g., 213C) was embedded through a hole in the septum stopper of the sparging port. The hole was sealed with waterproof silicone (General Electric).

Consolidated Bioprocessing ("CBP") Organism

The CBP organism Cuda was selected for these experiments based on its growth robustness with AFEX-CS under anaerobic conditions, ability to co-ferment six- and five-carbon sugars, ethanologenic yields (>40% maximum theoretical yield), and range of fermentation byproducts (acetate, formate, and to a lesser extent, $H_2$) that can serve as electron donors for the electricigenic bacterium (in the case of Gsu), as described in Example 1.

For these MFC experiments, *C. uda* was previously grown for 24 h in DB media with 0.2% cellobiose at 30° C. 36 mL (40% vol/vol) of cells were harvested by centrifugation, resuspended in DB medium containing the AFEX-CS, and inoculated into the anode chamber 204.

Electricigen

*G. sulfurreducens* ATCC 51573 (Gsu) was used as the electricigen. In this form, the Gsu is known to efficiently convert fermentation products (such as $H_2$, acetate, and formate) to electricity in MFCs and electrochemical cells. As the testing in Example 1 and below describes, growth rates of Gsu were unaffected in the presence of AFEX-CS. Furthermore, as shown in Example 1, this organism was capable of growing in co-culture with Cuda and coupling the conversion of all the fermentation byproducts to the reduction of a chemical electron acceptor such as fumarate. Thus, it was hypothesized that it could also couple the transfer of electrons from fermentation byproducts to the anode electrode of a MFC driven by AFEX-CS.

Testing

Conditions for growing Gsu in the MFC with acetate (1-6 mM) as electron donor were optimized as described in Example 2 and are described in detail under Procedures. These are conditions that enabled reproducible and relatively "fast" electricity production (i.e., starting approximately one (1) to two (2) hrs after inoculation of the MFC 118 with the electricigen Gsu) and also had the highest coulombic efficiencies (70 to 75% of acetate converted into electricity). Electron donor-to-current conversion efficiencies (coulombic efficiencies) are calculated using the EC-lab software from the integral of the current production curve over time to obtain the total coulombs transferred to the anode electrode during electricity production. The moles of electron donor (i.e., acetate) used by the electricigen are calculated by measuring its concentration in culture supernatant fluid samples by HPLC, as described in Example 1. The following equation is then used to calculate coulombic efficiency:

$$C_E = \frac{\int_0^t I dt}{Fbv_{an}\Delta c}$$

I=current in coulombs per second
t=time of experiment
F=Faraday's constant
b=the mole of electrons exchanged per mole of substrate
$v_{an}$=volume of the anode compartment
$\Delta c$=concentration of substrate in mol/L Controls with AFEX-CS and Gsu produced no current while controls with AFEX-CS/Gsu/acetate (3 mM) produced current with yields and coulombic efficiencies comparable to the Gsu/acetate (3 mM) (not shown).

Cuda controls growing alone with AFEX-CS also were included.

Consortia-Driven Electrochemical Cells

Figure 6:
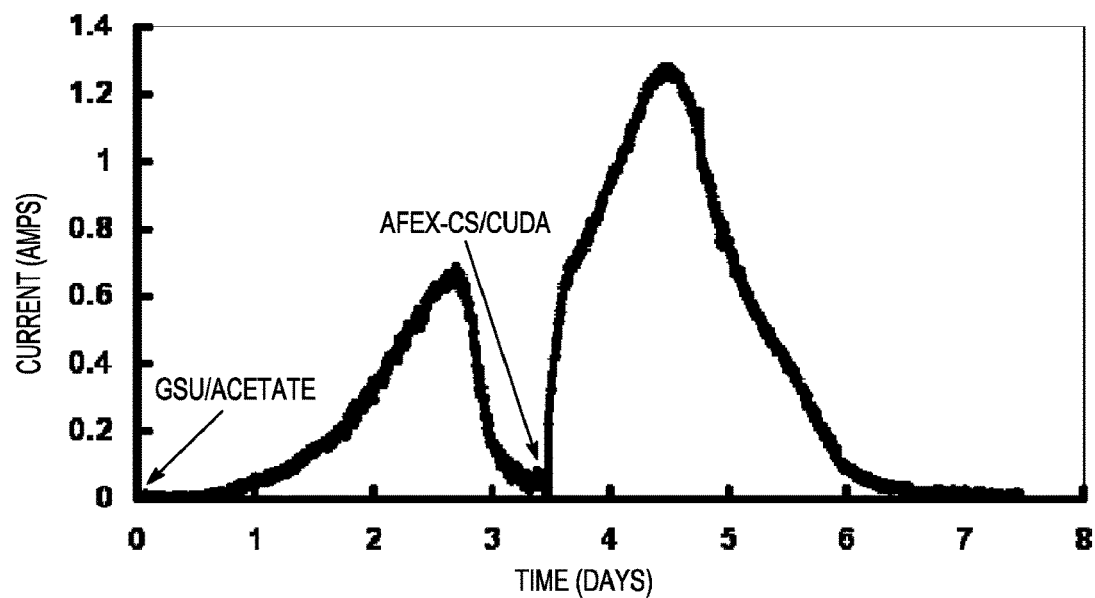
FIG. 6 shows current versus time for Gsu/acetate and after addition of AFEX-CS and Cuda according to various embodiments.

As shown in FIG. 6, when grown with three (3) mM acetate in a MFC Gsu produced current from acetate. When substantially all of the acetate was used, the current declined sharply. Once the current ceased, AFEX-CS and Cuda were added to the anode chamber and the current resumed immediately, reaching outputs approximately twice those obtained with the one (1) mM acetate. Ethanol and fermentation byproducts as well as any sugars remaining from the degradation of corn stover were measured daily.

Growth of the co-culture in the fuel cell was tested with and without nitrogen gas sparging. The use of nitrogen gas sparging facilitated the diffusion of organic acids through the anode biofilms and increased the yields of electricity. It also helped remove volatile solvents such as ethanol from the medium via gas stripping, thus removing possible solvent tolerance issues potentially capable of compromising the viability of Cuda and Gsu at the maximum theoretical production of ethanol desired for scaled-up applications.

As predicted, co-culturing converted much of the organic acids into electricity, but did not increase ethanol production. Fermentation was also inefficient, as some of the sugars were not used when compared to Cuda controls (grown alone with AFEX-CS) or co-cultures in which sparging was maintained throughout the experiment. Sparging of the medium with $N_2$ gas removed the ethanol as it was being produced, leading to a nearly 100% fermentation efficiency, an approximately 1.6-fold increase in electricity production, and removal of substantially all the formate and most of the acetate (at least about 15 mM) which were converted into electricity. The theoretical prediction estimates an approximately two-fold increase in ethanol production under these conditions (or the equivalent of more than 80% of the maximum theoretical yield).

Figure 7:
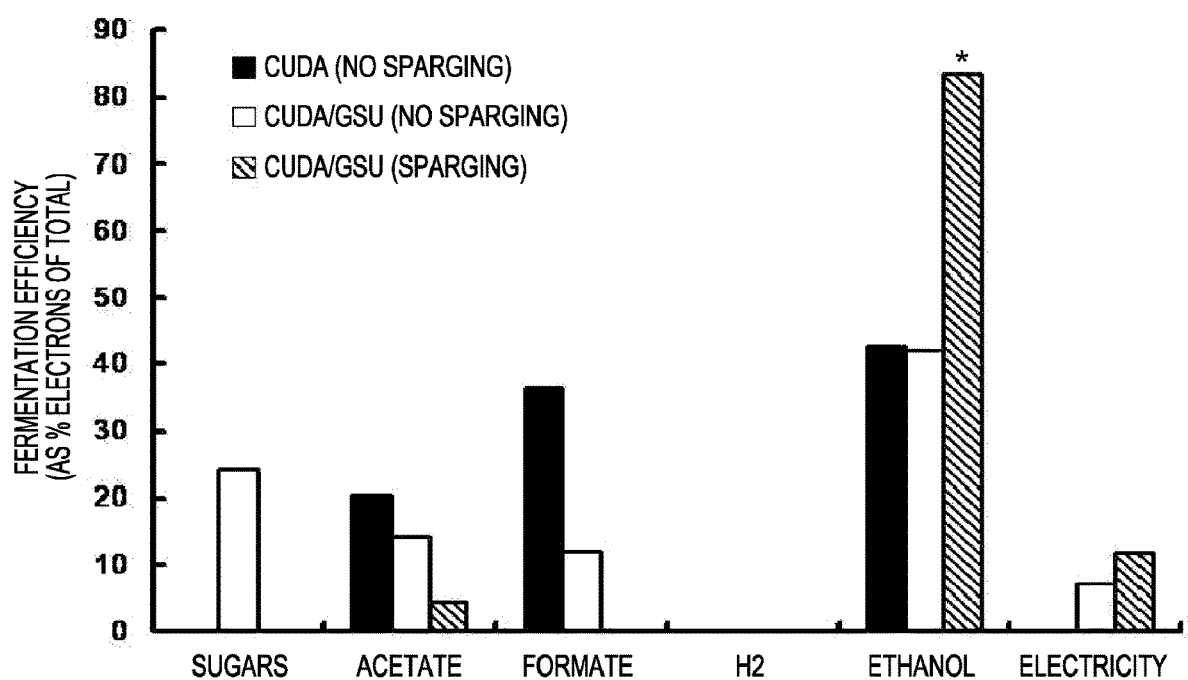
FIG. 7 is a bar graph showing fermentation efficiency of sugars, acetate, formate and hydrogen for Cuda alone, and in co-culture with Gsu, with and without gas sparging, according to various embodiments.

Cuda control cultures grown alone with AFEX-CS had a 100% fermentation efficiency with no detectable levels of soluble sugars in the medium and substantially all the theoretical electron content of the glucose and xylose components of the AFEX-corn stover (13.91 mmol of electrons) accounted for as acetate (21%), formate (37%), and ethanol (43%) (See FIG. 7).

Fermentation byproducts are known to negatively affect the rates of hydrolysis and fermentation by CBP organisms. Specifically, hydrogen is known to be a feedback inhibitor of cellulose hydrolysis, while organic acids quickly lead to media acidification, thereby decreasing growth robustness and fermentation yields.

Removal of the organic acids helped to support the growth of Gsu and current production and also prevented media acidification. In control cultures with Cuda and AFEX-CS alone, the pH dropped to 5.5 but remained close to neutral in the MFCs with the co-cultures or with Gsu alone. As a result of pH stability, cell viability and ethanol yields are expected to increase.

Strain Improvement for Increased Performance

Use of genetic engineering approaches for manipulation of the nature of the metabolic capabilities of the consortium partners were also investigated. Such approaches could potentially be used to customize the bioprocessing scheme and control the biofuel and electricity ratios produced using this platform. To accomplish this, a mutant of Gsu carrying a deletion in the genes encoding the uptake-hydrogenase Hyb of Gsu (hereinafter termed Gsu Hyb) was obtained from Dr. Coppi's Laboratory (University of Massachusetts, Amherst) and tested in co-culture with Cuda using AFEX-CS as substrate for Cuda and fumarate as terminal electron acceptor for Gsu Hyb. Controls with co-cultures of Cuda and genetically unaltered Gsu were used for comparison.

Hydrogen, even when present at very low levels or concentration (i.e., less than 1 mM) was determined to be preferentially used as an electron donor by Gsu anode biofilms during electricity production. A molecule of $H_2$ provides 2 electrons for power generation while acetate provides 8. Thus, we hypothesized that growth of Gsu and indirectly electricity generation could be increased when co-culturing a mutant of Gsu unable to use $H_2$ as an electron donor but able otherwise to use organic acids.

Figure 8:
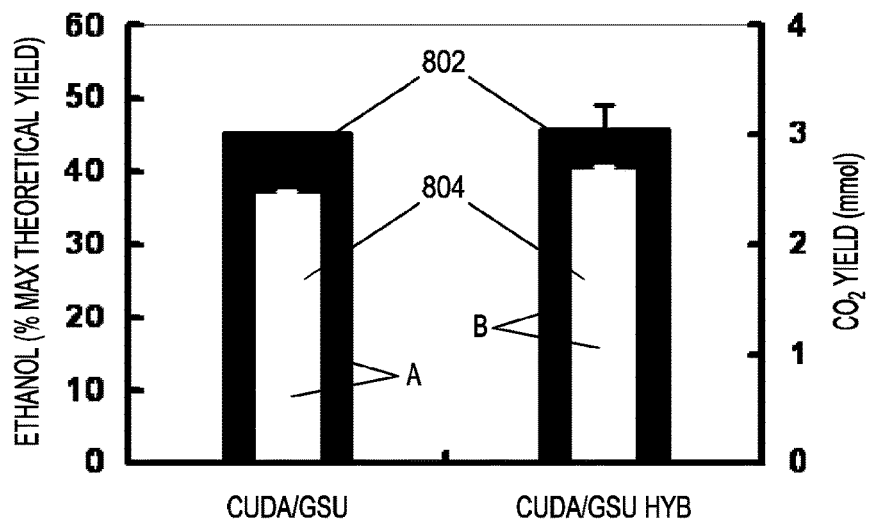
FIG. 8 is a bar graph showing $CO_2$ yield and ethanol yield of Gsu and a hydrogen uptake-deficient mutant of Gsu (Gsu Hyb) in co-cultures with Cuda according to various embodiments.

As bars 804 show in FIG. 8, although Cuda ("A") produces low levels of $H_2$ during fermentation, an approximately 1.2-fold increase in the growth of the Gsu Hyb mutant strain ("B) in consortium with Cuda was observed. Ethanol yields (802) remained substantially the same, however. These results demonstrate that it is possible to genetically engineer Gsu to manipulate the nature of the metabolic interaction, e.g., interspecies organic acid transfer, including with interspecies $H_2$-transfer, between the consortia partners to increase the overall energetic output of the system.

Taken together, these results demonstrate that fuel cells powered by an electricigen and a CBP organism can be effectively used as platforms for cellulosic ethanol production.

Procedure

The potential of the anode (working) electrode was controlled by the potentiostat, which was connected via wires (e.g., 213A, 213B and 213C) and alligator clips to the anode electrode, the cathode electrode and the reference electrode (e.g., 206, 207 and 216, respectively). The potentiostat was connected to a PC computer equipped with EC-lab software (Biol-Logic USA), which allowed real-time monitoring of the current produced at the anode electrode 202. The potentiostat 216 has four potentiostatic/galvanostatic boards so that four electrochemical cells 118 can be run simultaneously.

While the experiment was running, the anode and cathode chambers were sparged continuously with anaerobic gases by connecting gas distribution lines (Norprene tubing, Cole Parmer) to a Luer Lok hose end adapter (Fisher Scientific) and then to a 23-gauge needle 214 (Bencton Dickinson). Sterile 0.22-um syringe filters (Fisher Scientific) was placed between the Luer Lok hose adapter and the needle to sterilize the gases. Needles (e.g., 223A and 223B) were inserted through the septum stoppers of the sparging ports (e.g., 222A and 222B).

Gas outlets, e.g., 220A and 220B, were added to the anode and cathode chambers to release the $CO_2$ (produced during the conversion of organic acids into electricity by the electricigen) and the $H_2$ (produced from the electrochemical reaction of electrons and proton at the cathode), respectively, as well as any gas ($N_2$ and $CO_2$) used to sparge the growth medium (e.g., 208). The gas outlets were constructed using 12-cm metal cannulas (Popper), which were placed through stoppers (e.g., 218A and 218B) that sealed the top openings of the anode and cathode chambers. The top of the gas outlets (i.e., the cannulas) were each attached to a one-way female to male stopcock (Fisher Scientific) to open or close the respective gas outlets as needed.

Stirring also was achieved with ½"×⅛" octagonal stirbars (Fisher Scientific), which were located in the anode and cathode chambers, by placing the chambers on a 10-place stirplate (Fisher Scientific, IKAMAG).

The electrochemical cell experiments were run in the incubator (Described in Example 1) so that the temperature could be controlled to support the growth of the microbial consortia. The Cuda/Gsu consortium used in this testing was incubated at 30° C.

The electrochemical cell, set up as described above, but without the reference electrode or media, was autoclaved to sterilize it. The reference electrode was then sterilized by immersion in 70% ethanol, allowed to dry and added aseptically to the anode chamber. 90 mL of anaerobic DB media (prepared as described in Example 2) was added aseptically to the anode 204 and cathode 208 chambers (herein called DB media). Acetate (1 mM) was added to the anode 204 chamber to initiate the growth of the electricigen 120. The electrochemical cells are incubated at 30° C. and sparged with anaerobic gas mix ($N_2$:$CO_2$, 80:20) to buffer the pH of the medium at 7. Stirring was initiated at 500 rpm.

An electricigen 120 was grown as a film on the anode electrode 208 located in the anode chamber 202. The anode electrode 202 was poised at the desired potential (an anode potential of +0.24V was used to make a cathode-unlimited system) with respect to the Ag/AgCl reference electrode 214 using a potentiostat 212. In this way, a cathode-unlimited system was used for controlled and reproducible results. The system was allowed to equilibrate for a minimum of approximately two hours.

The electricigen 120 (Gsu) was subcultured at approximately 30° C. in 100-ml of standard anaerobic DB media supplemented with the desired concentration of electron donor (e.g. 10-30 mM acetate) and electron acceptor (e.g., 40-50 mM fumarate). Cells from 36 ml (or 40% of the volume of the anode chamber 204) of early stationary phase cultures (e.g., those that have ceased exponential growth) of the electricigen 120 Gsu were harvested by centrifugation (6,000 rpm, 8 min, fixed rotor, 25° C.), washed once with DB media without acetate or fumarate, and resuspended in DB media. The cells were then injected aseptically into the anode chamber 204 with a syringe and a needle and through the side-arm septum port 222. Samples of the media in the anode chamber 204 were periodically removed with a syringe and a needle and through the side-arm septum port 222 for HPLC analyses of organic acids and sugars.

Current production was initiated after approximately 12-18 hours had passed from the initiation of the experiment by adding approximately one (1) mM of acetate as the electron donor. The current increased exponentially in the next 24-48 hr until substantially all the acetate was used by the electricigen 120. Current generation was determined to be directly related to the growth of the electricigen as a film on the anode electrode 202. In the examples presented here, substantially all the acetate was consumed in 40-48 h after measurable current was initiated and an orange electricigenic film 120 was visually apparent on the anode electrode 202. Once the acetate was used, the current declined sharply.

The CBP organism and the AFEX-CS were added to the anode chamber once the current reached zero (0) mA.

Example 4

The equipment and starting materials as described in the above examples were used herein. FIGS. 9-13 T show how conversion efficiencies and current yields are affected depending on the type of inoculation procedure followed.

Sequential Inoculation

Figure 9:
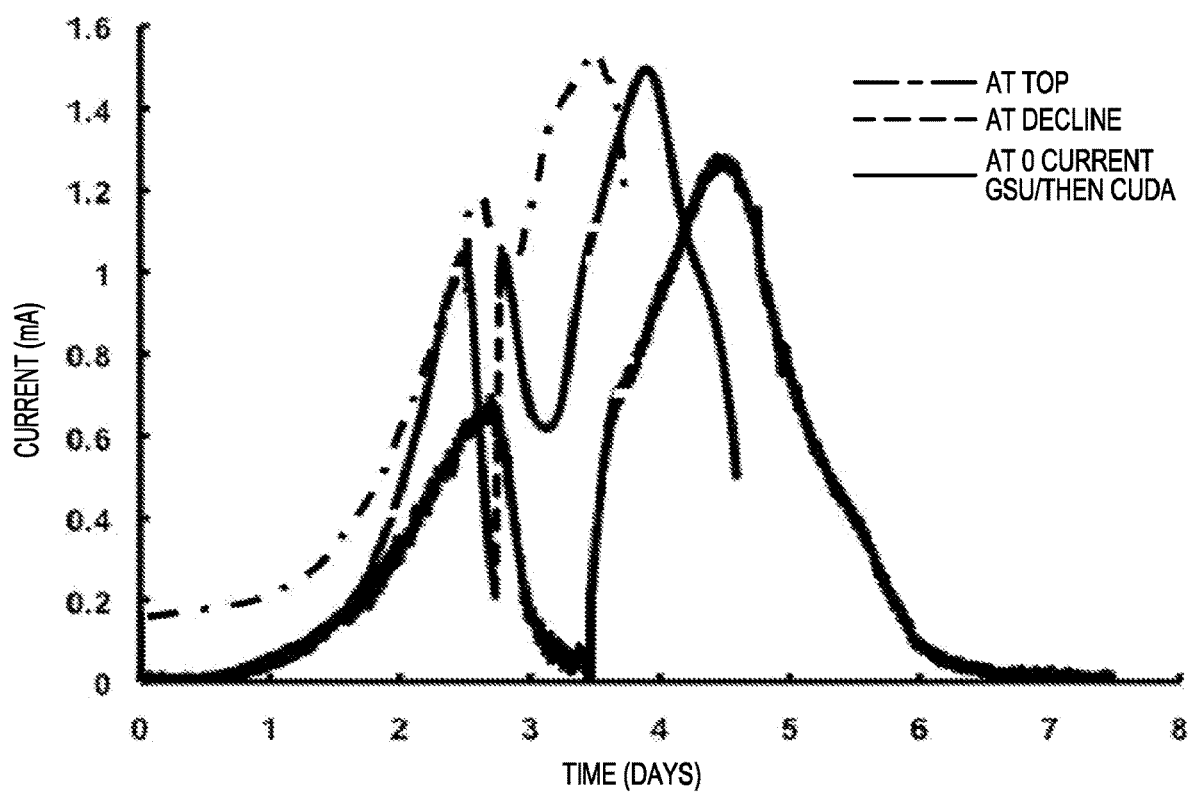
FIG. 9 shows current versus time for Gsu/acetate sequentially inoculated with Cuda and AFEX-CS at maximum current, zero current, and during a declining current according to various embodiments.

In one experiment, a CBP organism (Cuda) was added to a film of an electricigen (Gsu) (which was pre-grown on the anode electrode with 1 mM acetate) at the top of current production, during current decline once all of the acetate has been used, or when current ceased (0 mA), as shown in FIG. 9. Sparging was used to facilitate mixing while the electricigen was forming a film on the anode. Once the CBP organism was added, the sparging and outlet ports of the anode chamber were closed.

In the experiments shown in FIG. 9 ethanol yields in the range of 40-50% and yields of conversion of fermentation byproducts into electricity in the range of 8-13% of the maximum theoretical yields were reached, respectively, after 24, 26, and 22 h. of inoculation with the insolubles and the CBP organism. This contrasts with the more than 80% ethanol yields reached when sparging was maintained throughout the experiment, as shown in FIG. 8, to evaporate the ethanol produced by the CBP organism and substantially minimize growth inhibition of the CBP organism due to the accumulation of ethanol.

These results show that biocatalysts, such as *C. uda* and the AFEX-CS, can be added sequentially at any given time during current production by the electricigen. In this example, current recovery was shown when the AFEX-CS and *C. uda* were added at various times, when Gsu is at its maximum current ('at top', dashed line), when it is half way in decline ('at decline', double line) and when current has reached 0 mA ('at 0 current', thick black line). (See FIG. 9).

These results also show that improving the ethanol tolerance of the CBP organism is expected to substantially increase ethanol yields at levels more than 80% of the maximum theoretical.

Substantially Simultaneous Inoculation

In this experiment, biocatalysts (Cuda and Gsu) were added substantially simultaneously, together with the insolubles (AFEX-CS) into the anode chamber. One (1) mM of acetate was added to one of the inoculums to jump start the growth of Gsu's growth. Sparging was maintained throughout the experiment to evaporate the ethanol and promote growth of the electricigen on the anode electrode.

Figure 10:
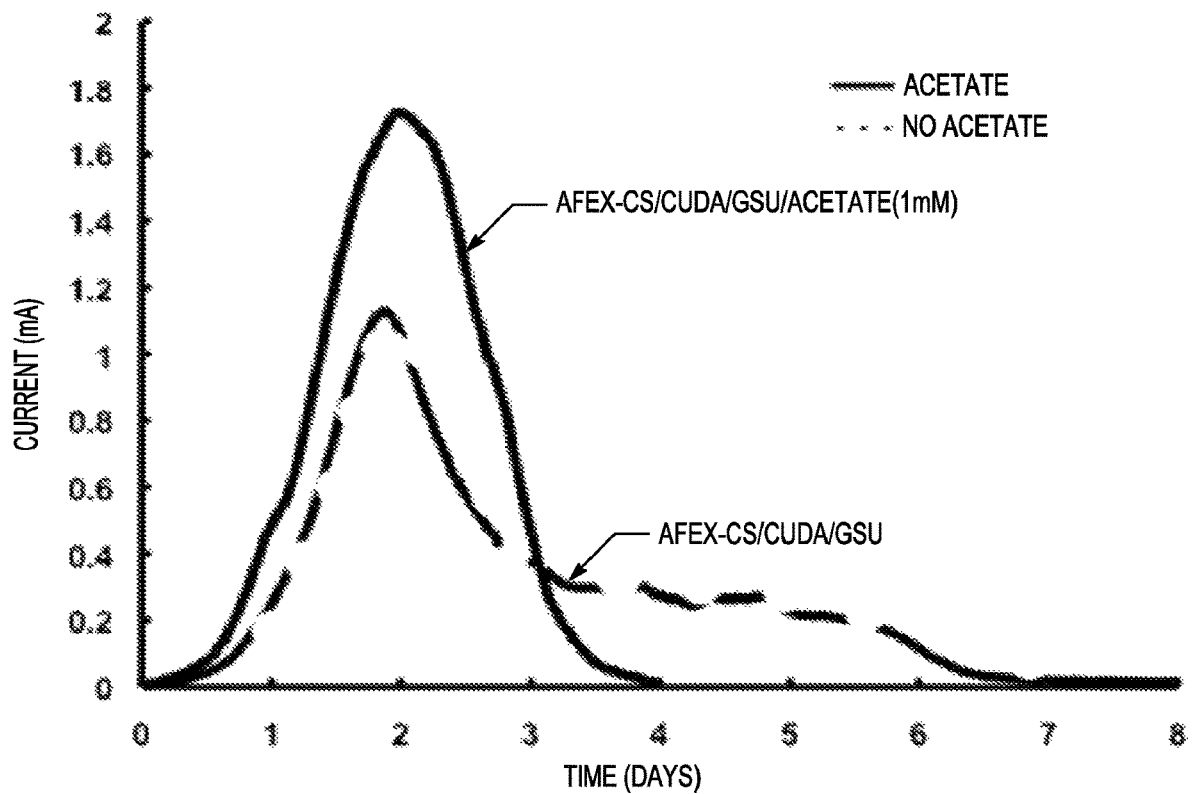
FIG. 10 shows current versus time for simultaneous inoculations of AFEX-CS/Cuda/Gsu with acetate (1 mM) and without acetate according to various embodiments.

As FIG. 10 shows current generation starts after 2-4 hours of incubation and increases exponentially after 9-14 h in cultures with or without acetate supplementation, respectively. Maximum currents are reached after 40-46 h in both experiments.

Figure 11:
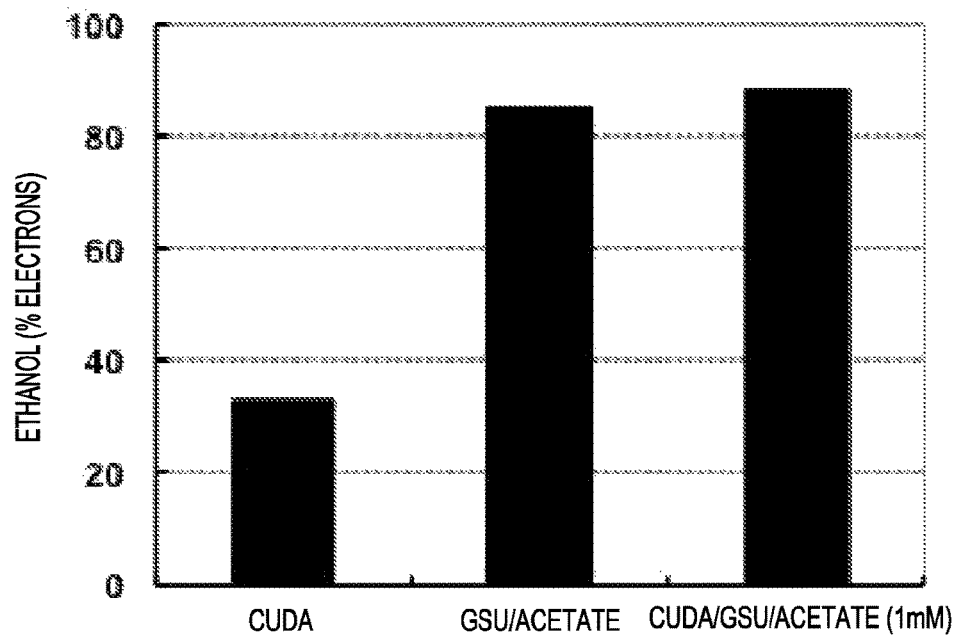
FIG. 11 is a bar graph showing ethanol yield for Cuda, Cuda/Gsu and Cuda/Gsu/acetate (1 mM) according to various embodiments.

FIG. 11 shows the ethanologenic efficiency of the organisms tested in FIG. 10, which are of at least about 80% of the maximum theoretical yield, with all the fermentation byproducts (acetate, formate, lactate and $H_2$) having been converted into electricity. This is in contrast to the ethanologenic efficiency of controls of Cuda alone, also shown in FIG. 11, which produced less than 40% of the maximum theoretical yield.

Figure 12:
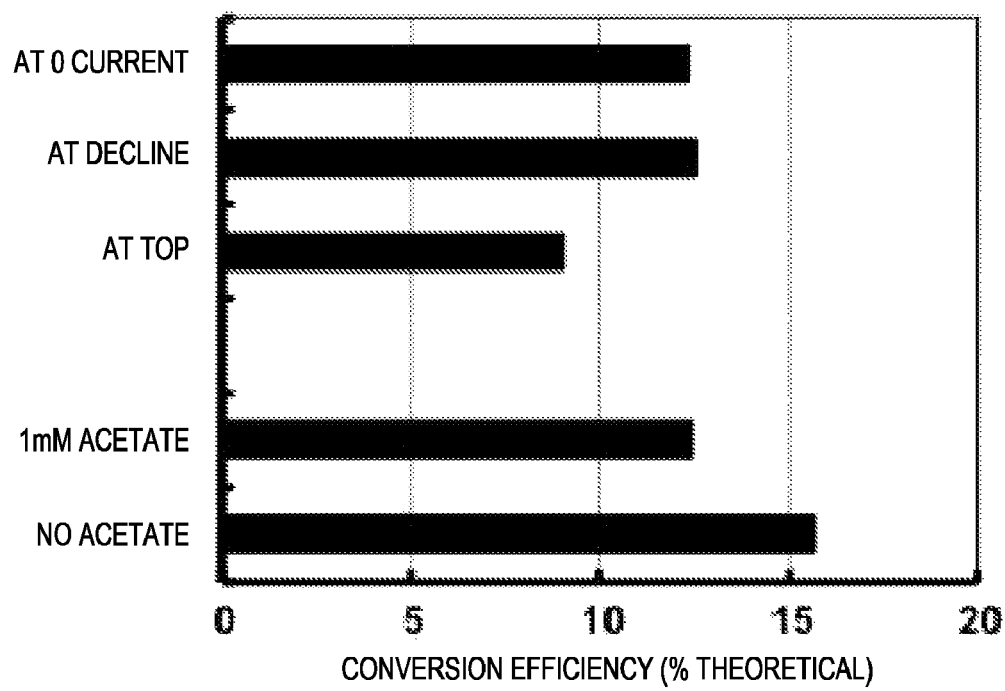
FIG. 12 is a bar graph showing current yields (as conversion efficiency) for the sequential and simultaneous inoculations of FIGS. 10 and 11, respectively, according to various embodiments.

FIG. 12 is a bar graph showing the conversion efficiency of fermentation byproducts into electricity for the sequential and simultaneous inoculations of FIGS. 9 and 10, respectively, in embodiments of the present invention.

Figure 13:
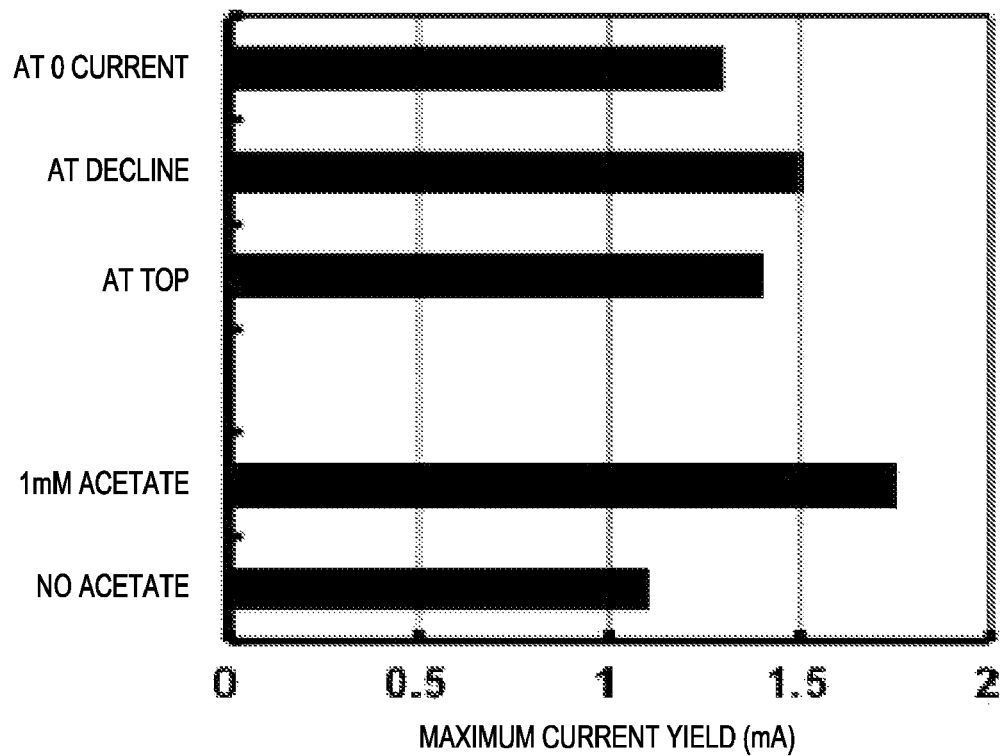
FIG. 13 is a bar graph showing maximum current yield for the sequential and simultaneous inoculations of FIGS. 10 and 11, respectively, according to various embodiments.

FIG. 13 is a bar graph showing maximum current yields for the sequential and simultaneous inoculations of FIGS. 9 and 10, respectively, in embodiments of the present invention These results show that simultaneous addition of the biocatalysts does not affect conversion efficiencies. Additionally, supplementation with acetate allowed Gsu to generate current more quickly and increased current yields. Adding components simultaneously also minimizes disruptions to the bioprocessing reaction and reduces costs associated with the set up of the bioreactor.

Conclusions

As FIGS. 9-13 show, simultaneous inoculation had a higher efficiency at converting fermentation byproducts into electricity as compared to sequential inoculation, but was a slower process (reduced rates per day). Addition of acetate is slightly less efficient but faster. Thus, inoculation strategies can be used to customize the yields and rates of electricity generation.

Inoculation at mid-point of current decline appears to be optimal for both parameters when using sequential inoculation.

Example 5

Identification of a Glycerol-Fermenting Microbial Catalyst.

Gram-positive bacteria, *Clostridia*, (from culture collection identified in Example 1) was selected for use in ethanologenic fermentation of glycerol. Cultures were supplemented with 0.6% yeast extract to mimic the reported sugar content of biodiesel wastewater, which also contributes to the fermentative metabolism, ethanologenesis, and generation of fermentation byproducts.

Among the more than 10 species tested, only *C. cellobioparum* (Cce) grew well, consumed substantially all the glycerol (0.25% (w/v) from solution and fermented it to ethanol, acetate, lactate and formate and $H_2$. See FIGS. 15A and 15B. Ethanol was the major fermentation product (ca. 40% of maximum theoretical yield) and was not produced in the same medium without glycerol, thus confirming it was produced from glycerol fermentation. Cce's growth rates and yields were naturally robust, suggesting that this organism is naturally tuned for fermentative growth and ethanologenesis from glycerol. It also produced only fermentation byproducts that can serve as electron donors for the electricgen *G. sulfurreducens* (Gsu). For this reason, Cce was selected as the fermentative catalyst for the microbial platform.

Stimulation of Glycerol Fermentation in the Co-Culture

Figure 15A:
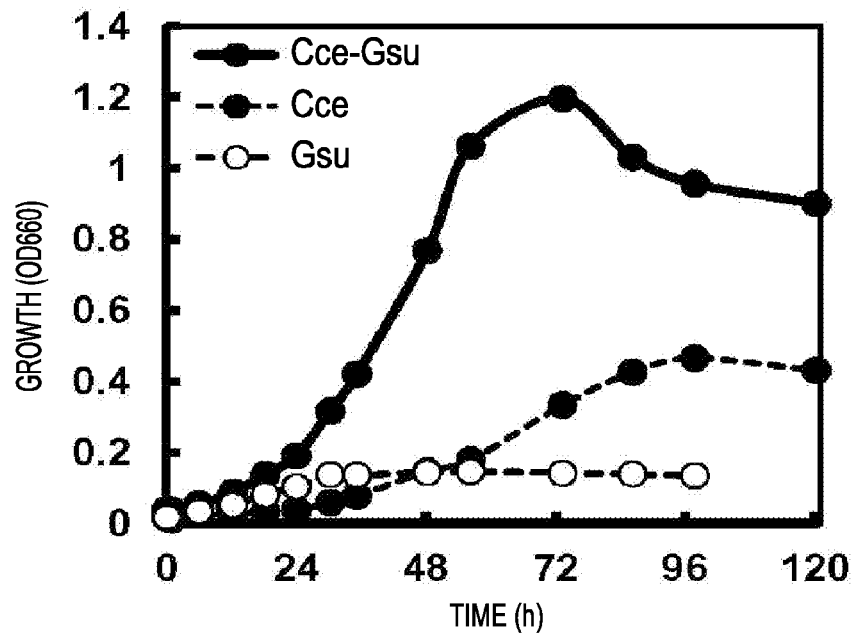
FIG. 15A is a graph showing glycerol growth of Gsu, *C. cellobioparum* (Cce), and a co-culture comprising Cce-Gsu, over time according to an embodiment.
Figure 15B:
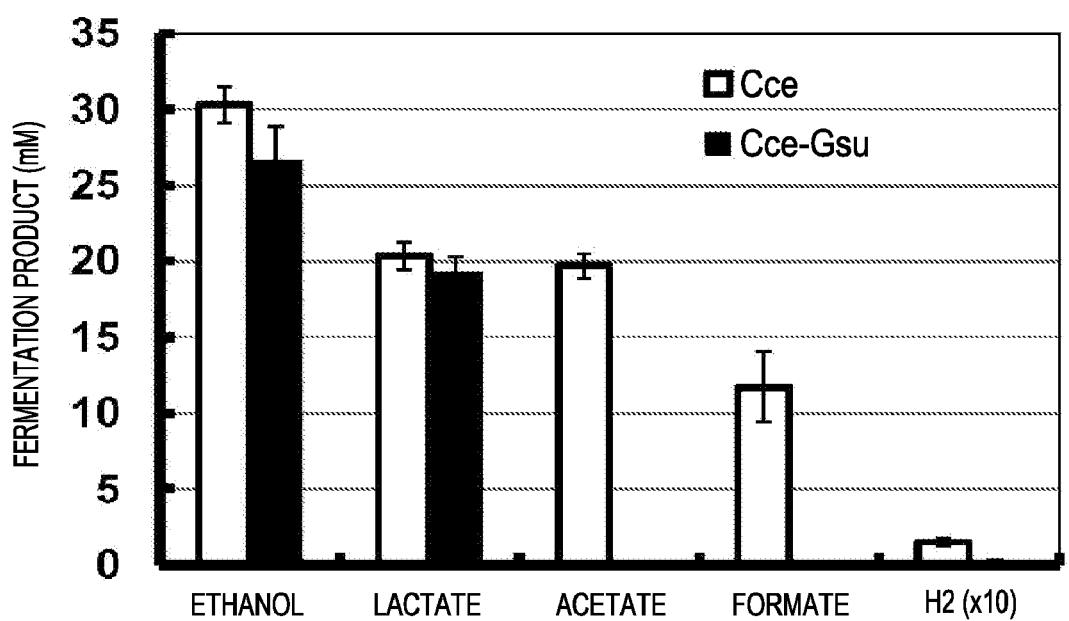
FIG. 15B is a bar graph showing fermentation production for Cce and a co-culture comprising Cce-Gsu with ethanol, lactate, acetate, formate and hydrogen according to various embodiments.

Removal of $H_2$ and organic acids during coculture of Cce with Gsu greatly stimulated fermentative growth as shown in FIG. 15A. The acetate, formate and $H_2$ were removed by Gsu by providing fumarate as an electron acceptor. However, lactate remained in the fermentation broth. As a result, lactate accumulation dropped the pH of the fermentation broth to 6.3, which also negatively affected the growth of Gsu and Cce.

Strain Improvement by Adaptive Evolution

Figure 16A:
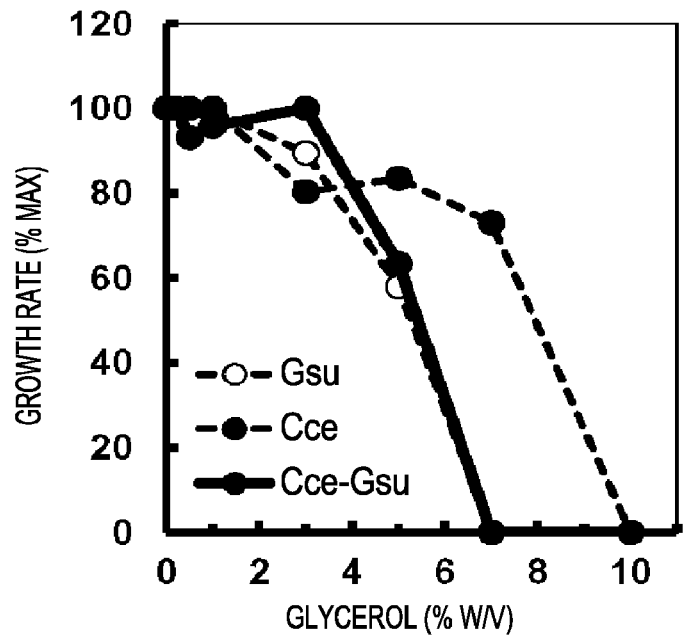
FIG. 16A is a graph showing growth rate for Gsu, Cce and Cce-Gsu in glycerol according to various embodiments.
Figure 16B:
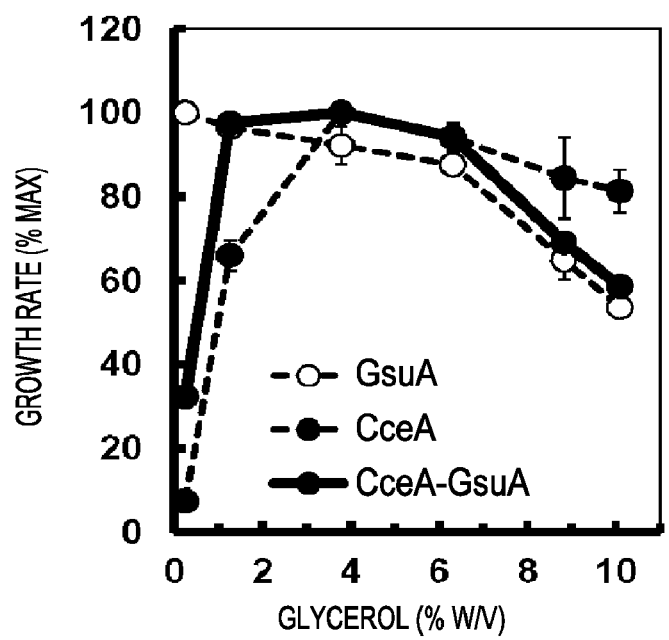
FIG. 16B is a graph showing growth rate for an alcohol-tolerant strain of Gsu (GsuA), a glycerol-tolerant strain of Cce (CceA) and a co-culture comprising CceA-GsuA in glycerol according to various embodiments.
Figure 16C:
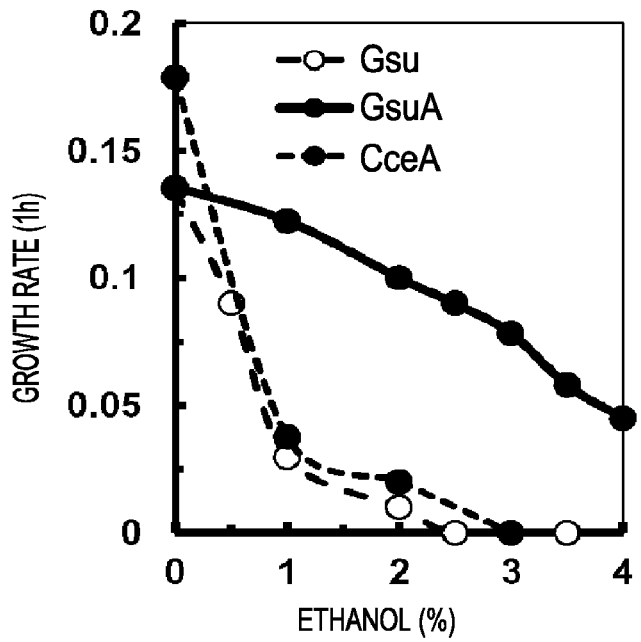
FIG. 16C is a graph showing growth rate for Gsu, GsuA and CceA in ethanol according to various embodiments.

Glycerol tolerance of the microbial catalysts was also tested, with the results shown in FIGS. 16A-16C. The fermentative catalyst, Cce, grew with up to 7% (w/v) glycerol while maintaining growth rates of at least 75% of the maxima (FIG. 16A). After successive passages with increasing concentrations of glycerol, an alcohol-tolerant strain of Cce (CceA) adapted for growth with 10% glycerol (FIG. 16B) was produced. The growth of the electrogenic partner, Gsu, was inhibited at 7% glycerol in both the monoculture and the coculture (FIG. 16A).

Robustness of Gsu was improved by selecting for variants that grew with inhibitory (1%) concentrations of ethanol (FIG. 16C). After six months of successive passages at increasing ethanol concentrations, an alcohol-tolerant strain of Gsu (GsuA) was isolated, which tolerated 4% ethanol (FIG. 16C). GsuA also increased its glycerol tolerance to 10% glycerol in both the monoculture and CceA coculture (FIG. 16B).

Despite the improved glycerol tolerance in CceA, glycerol consumption reached a plateau once ethanol production reached levels ca. 0.5%. Hence, the alcohol tolerance of CceA was investigated. Strain sensitivity to ethanol concentrations in this range was confirmed (FIG. 16C).

Coupling Glycerol Fermentation to Current Production in a BEC.

The coupling of glycerol fermentation and ethanologenesis to current production was demonstrated in a BEC driven by the CceA-GsuA co-culture. For these experiments, GsuA was incubated at 30° C. in the anode chamber of an anoxic, dual-chamber, H-type MFC equipped with graphite rod electrodes poised at a constant potential of 240 mV. This anoxic, poised system maintained consistency between different fuel cells, removed any potential limitations resulting from electron transfer at the cathode, and eliminated the possibility of oxygen intrusion into the anode chamber that might support aerobic growth.

Figure 17:
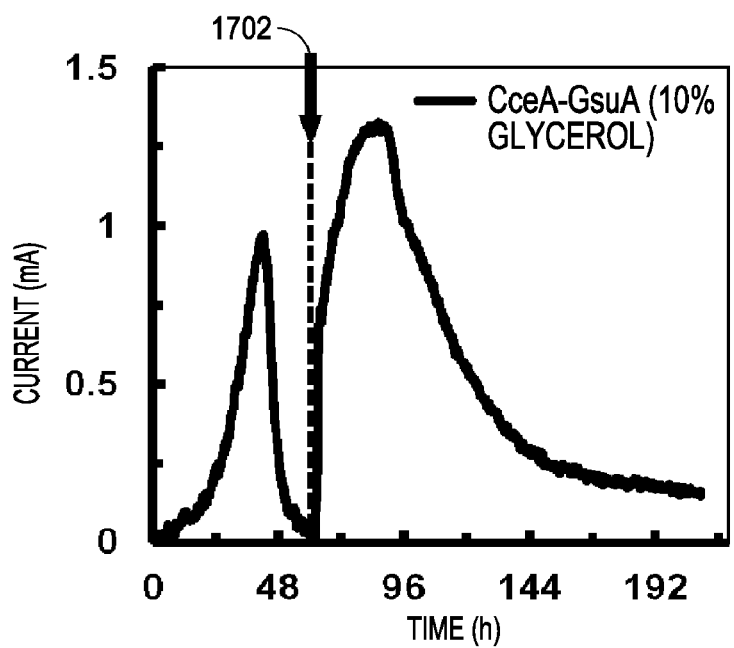
FIG. 17 is a graph showing current versus time for CceA-GsuA grown with 10% glycerol according to an embodiment.

When 1 mM acetate was added to the medium in the anode chamber, the current rapidly increased to ca. 1 mA and then declined as the acetate was depleted (FIG. 17). The coulombic efficiency of GsuA was comparable to Gsu (89.8±3.3%), demonstrating that evolving alcohol tolerance had not affected its electrogenic activity.

Once current production declined, CceA was added to the GsuA anode chamber at location 1702 and current production resumed. Glycerol consumption and ethanol production were stimulated (2.8- and 1.4-fold, respectively) in the BECs driven by the co-culture of CceA-GsuA, as compared to CceA controls.

As observed previously, ethanol production reached a plateau once it reached growth inhibitory concentrations (0.6%). Although current (3.2±0.3 mmol of electrons) was produced from fermentation byproducts, it declined before all of the acetate and formate was removed. Because GsuA grows well at these alcohol concentrations, it is unlikely that the inefficient removal of electron donors was caused by ethanol inhibition (FIG. 16C). However, lactate also accumulated in the BEC broth and acidified the medium (final pH of 5.5). In fact, the electrogenic efficiency of GsuA declined once the pH began to drop below 6. These results demonstrate that BECs can be used to stimulate glycerol fermentation while generating ethanol and current.

Conclusion

The composition of the final, 80% concentrated crude glycerin varies. See, for example, Suehara, K. et al. Biological treatment of wastewater discharged from biodiesel fuel production plant with alkali-catalyzed transesterification. *J. Biosci. Bioeng.* 100, 437-442, doi:S1389-1723(05) 70489-8 [pii] 10.1263/jbb.100.437 (2005) and Williams, P. R., Inman, D., Aden, A. & Heath, G. A. Environmental and sustainability factors associated with next-generation biofuels in the U.S.: what do we really know? *Environ. Sci. Technol.* 43, 4763-4775 (2009), both of which are incorporated herein by reference. Based on these reports, calculations understood by those skilled in the art were made to determine the content of glycerol and alcohol in glycerin wastewater (after acid pretreatment to remove oil and precipitate the soap and salts). These calculations showed that glycerin wastewater likely contains about 10 to about 20% glycerol and about 2 to about 6% alcohol. These values are within the ranges reported for laboratory-treated raw glycerol solutions derived from several biodiesel plants. See, for example, Moon, C., Ahn, J. H., Kim, S. W., Sang, B. I. & Um, Y. Effect of biodiesel-derived raw glycerol on 1,3-propanediol production by different microorganisms. *Appl. Biochem. Biotechnol.* 161, 502-510, doi:10.1007/s12010-009-8859-6 (2010), which is incorporated herein by reference. As such, these values provide confirmation that the minimum alcohol target has been reached for GsuA and the glycerol target for both strains.

Adaptively evolving the catalysts to improve their alcohol tolerance is expected to further improve performance. As shown in this example, an alcohol-tolerant strain of Gsu, termed GsuA, was evolved and grew in the presence of 4% (v/v) ethanol and tolerated 10% glycerol loadings. It is expected that catalyst performance can be even further enhanced via adaptive evolution and/or genetic engineering to further increase alcohol and glycerol tolerances. Such approaches are also expected to co-evolve glycerol productivity and ethanol yields.

Example 6

Cultures from Example 5 were transferred in the stationary phase, when error-prone DNA Polymerase IV is expressed and the mutation rate is high. See, for example, Tompkins, J. D. et al. Error-prone polymerase, DNA polymerase IV, is responsible for transient hypermutation during adaptive mutation in *Escherichia coli. J. Bacteriol.* 185, 3469-3472 (2003), which is incorporated herein by reference. Transfer during this phase increases the potential for mutant variants to arise and accelerates an otherwise slow process.

Gsu was transferred in this manner at higher concentrations of ethanol and variants growing with 4.5% ethanol have been demonstrated. Thus, this approach is expected to be effective to reach a targeted industrial concentration of 6% in glycerin wastewater or higher.

Example 7

CceA was transferred in this manner at higher concentrations of ethanol and variants growing with 2% ethanol have been demonstrated.

These results suggest that the approach being used is rapid and effective. Inasmuch as ethanol sensitivity limited glycerol fermentation by CceA, alcohol tolerance is also expected to increase fermentation robustness and ethanol yields from 10% (w/v) glycerol.

Example 8 (Prophetic)

The hypothesis noted in Example 7 will be monitored by periodically growing the alcohol-tolerant variants in cultures with 10% glycerol and measuring glycerol consumption and ethanol production in the fermentation broth.

Example 9 (Prophetic)

Growth of the transferred cultures (such as Gsu in Example 6 and CceA in Example 7) will be monitored as optical density of the cultures at 660 nm using a spectrophotometer. Once growth is observed at a target alcohol concentration, the cultures will be maintained through several passages in the same ethanol concentration until growth rates and yields return to native, unchallenged levels or until they stabilize.

At this point, aliquots of cultures containing the adapted variants will be plated to isolate individual colonies, corresponding to clonal variants. Approximately 10 colonies will be inoculated in fresh liquid medium with ethanol to identify the fastest-growing variants. After repeated passages in exponential phase, the fastest growers are enriched and will be preserved anaerobically at −80° C. in dimethyl sulfoxide (DMSO). The variant with the best growth rates and yields will be transferred to the next concentration increment (0.5%) to initiate a new round of evolution. The experiment will end when variants no longer arise.

It is expected that concentrations of ethanol at or above the 6% target will be achieved.

Example 10 (Prophetic)

Additional testing will include testing of industrial solid loadings (above 2%), of other CBP organisms and electricigen combinations, strain improvement through genetic engineering and adaptive evolution, testing of other substrates, and producing biofuels other than ethanol.

Conclusion

The embodiments described herein provide an economically and environmentally superior consolidated bioprocessing technology for ethanol and electrical power production from substrates in a bioelectrochemical cell, such as a microbial fuel cell, as compared to conventional microbially-catalyzed consolidated bioprocessing. Based on current estimates, CBP bioprocessing is expected to reduce the cost of cellulosic ethanol by as much as 51%, and provide ethanol yields close to 90% (or more) of the maximum theoretical yields, while the co-fermentation of both glucose and xylose is expected to reduce the final fuel cost by at least an additional six (6)%. CBP processing is expected to reduce the cost of biodiesel and provide similar ethanol yields, while the co-fermentation of both glucose and xylose is expected to reduce the final cost by at least an additional six (6)%.

In one embodiment, a maximum yield of ethanol above 80% and a substantially complete co-fermentation of six- and five-carbon sugars while producing electricity as a value-added product is produced. In one embodiment, feedstock processing and diversification strategies are integrated in a single step fermentation, with removal of non-valued, inhibitory products for power co-generation. In one embodiment, strain improvement by genetic engineering and direct evolution is utilized.

In one embodiment, a single-chambered electrochemical bioreactor system can be used for biofuel production, which can be constructed using commercially available bioreactors and fermentors.

Unlike conventional methods, embodiments described herein decouple bioenergy production from the food supply and reduces processing costs through the use of low cost lignocelluloses substrates, single-step hydrolysis and fermentation, and conversion of low-value fermentation byproducts into electricity. In one embodiment, the conversions take place in a single bioreactor or vessel, thereby minimizing costs associated with chemical separations of fermentation products and development of secondary processing units.

The embodiments described herein, which directly generate electricity and/or ethanol from glycerin-containing water, such as a glycerin stream from biodiesel product, provide an inexpensive alternative to glycerin wastewater refining. The process not only provides for treatment of the glycerin wastewater, but also generates biofuels and energy, which can be sold, transported or used in the biodiesel production facility.

Embodiments described herein provide a competitive consolidated bioprocessing technology for biofuel and electrical power production in a microbial fuel cell or electrochemical cell. The novel processes described herein integrate feedstock processing and diversification strategies, single step hydrolysis and fermentation, use of fermentation byproducts for electricity generation, and microorganism strain improvement through genetic engineering and direct evolution.

In one embodiment, the novel system and methods described herein are customized for other types of biomass and/or other types of biofuel, by selecting a particular CBP organism and electricigenic partner. In one embodiment, genetic engineering and adaptive evolution of these bacterial partners is used to modulate biofuel and electricity production rates and yields.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. For example, although the fermentation byproducts have been described as including primarily organic acids and/or primarily hydrogen, it is to be understood that other fermentation byproducts may also be useful herein. Therefore, it is manifestly intended that embodiments of this invention be limited only by the claims and the equivalents thereof.

What is claimed is:

1. A method comprising:
   a consolidated hydrolyzing and fermentation step for converting a biomass to a biofuel with a mesophilic first organism in an anode chamber, wherein the mesophilic first organism comprises at least *Cellulomonas uda* (Cuda), and the anode chamber contains an anode electrode, further wherein the converting step produces fermentation waste byproducts;
   transferring electrons in the byproducts to the anode electrode with a second organism to produce a film; and
   allowing the film to catalytically split the electrons and protons, wherein the electrons flow towards a cathode electrode to produce electricity and the protons permeate a proton-exchange membrane connecting the anode chamber and a cathode chamber, wherein the electrons and protons react to produce hydrogen gas, wherein substantially all the fermentation waste byproducts are converted to electricity.

2. The method of claim 1 wherein the second organism is an electricigen comprising *Geobacter sulfurreducens* (Gsu).

3. The method of claim 2 where the first and second organisms are added sequentially.

4. The method of claim 2 wherein the first and second organisms are added substantially simultaneously.

5. The method of claim 2 wherein the mesophilic first organism further comprises one or more additional cellulomonad organisms and/or one or more clostridia organisms.

6. The method of claim 5 wherein the one or more additional cellulomonad organisms are selected from *Cellulomonas biazotea, Cellulomonas cartae, Cellulomonas gelida, Cellulomonas fimi, Cellulomona flavigena*, and combinations thereof, and the one or more *clostridium* organisms are selected from *Clostridium hungatei, Clostridium papyrosolvens, Clostridium longisporum, Clostridium populeti, Clostridium cellulovorans, Clostridium phytofermentans, Clostridium lentocellum, Acetivibrio cellulolyticus, Ruminococcus albus*, and combinations thereof.

7. The method of claim 1 further comprising applying a potential to the anode electrode.

8. The method of claim 1 wherein the biofuel is ethanol.

9. The method of claim 1 wherein the biomass is a non-food biomass.

10. The method of claim 9 wherein the non-food biomass is corn stover.

11. The method of claim 1 wherein a chemical reaction occurs in the cathode chamber.

12. A method comprising:
    a consolidated hydrolyzing and fermentation step for converting a biomass to a product with one or more mesophilic consolidated bioprocessing organisms in a reaction chamber containing the biomass, an anode electrode and a cathode electrode, wherein at least one of the one or more mesophilic consolidated bioprocessing organisms are *Cellulomonas uda* (Cuda), and with a second organism comprising an electricigen disposed on the anode electrode, wherein the converting step produces fermentation waste byproducts;
    transferring electrons in the fermentation waste byproducts to the anode electrode through the second organism comprising an electricigen; and
    allowing the second organism to catalytically split electrons and protons from the fermentation waste byproducts, wherein the electrons flow from the anode electrode to the cathode electrode to produce electricity and the electrons and the protons react to produce hydrogen gas, wherein at least a portion of the byproducts are the fermentation waste byproducts and wherein substantially all the fermentation waste byproducts are converted to electricity.

13. The method of claim 12 wherein the reaction chamber comprises a single chamber, wherein the single chamber further comprises a reference electrode.

14. The method of claim 13 wherein the anode electrode, the cathode electrode and the reference electrode are electronically connected to each other and to an external electric current which creates a potential between the anode electrode and the cathode electrode.

15. The method of claim 12 wherein the reaction chamber comprises an anode chamber and a cathode chamber, wherein the anode electrode is located in the anode chamber and the cathode electrode is located in the cathode chamber, wherein the anode and cathode chambers are separated by a proton exchange membrane, wherein the anode chamber further comprises a reference electrode.

16. The method of claim 12 wherein the second organism is disposed on the anode electrode as a film.

17. The method of claim 12 wherein the electrons and the protons react at the cathode electrode.

18. The method of claim 12 wherein the product is a biofuel.

19. The method of claim 18 wherein the biofuel is ethanol.

20. The method of claim 12 wherein the one or more mesophilic consolidated bioprocessing organisms comprise one or more additional cellulomonad organisms and/or one or more clostridia organisms.

21. The method of claim 20 wherein the one or more additional cellulomonad organisms are selected from *Cellulomonas biazotea, Cellulomonas cartae, Cellulomonas gelida, Cellulomonas fimi, Cellulomona flavigena*, and combinations thereof, and the one or more *clostridium* organisms are selected from *Clostridium hungatei, Clostridium papyrosolvens, Clostridium longisporum, Clostridium populeti, Clostridium cellulovorans, Clostridium phytofermentans, Clostridium lentocellum, Acetivibrio cellulolyticus, Ruminococcus albus*, and combinations thereof.

22. A method comprising:
a consolidated hydrolyzing and fermentation step for converting a non-food biomass comprising biodiesel and/or glycerin-containing water to a biofuel with a mesophilic first organism in an anode chamber, wherein the mesophilic first organism is not *Clostridium cellulolyticum* and the anode chamber contains an anode electrode, further wherein the converting step produces fermentation waste byproducts;
transferring electrons in the byproducts to the anode electrode with a second organism to produce a film; and
allowing the film to catalytically split the electrons and protons, wherein the electrons flow towards a cathode electrode to produce electricity and the protons permeate a proton-exchange membrane connecting the anode chamber and a cathode chamber, wherein the electrons and protons react to produce hydrogen gas, wherein substantially all the fermentation waste byproducts are converted to electricity.

* * * * *

UNITED STATES PATENT AND TRADEMARK OFFICE
CERTIFICATE OF CORRECTION

PATENT NO. : 10,686,205 B2
APPLICATION NO. : 15/589950
DATED : June 16, 2020
INVENTOR(S) : Gemma Reguera, Allison Spears and Jenna Young It is certified that error appears in the above-identified patent and that said Letters Patent is hereby corrected as shown below:

On the Title Page

In the References:
Page 2/References/Column 2/Line 14 Lau, et al: reads as "AFEX-trealed corn" and should read as "AFEX-treated corn"

In the Specification

Column 5/Line 17: reads as "waste s" and should read as "wastes"

Column 7/Line 20: reads as "value added" and should be read as "value-added"

Column 21/Line 28: reads as "scalable up 10, 100 to 1000 times or more" and should read as "scalable up to 10 times, or up to 100 to 1000 times, or more,"

Column 26/Lines 30-31: reads as "Elec-trosynthesis))," and should read as "(Elec-trosynthesis)),"

Column 30/Line 38: reads as "strain ("B")" and should read as "strain ("B")"

Column 32/Line 14: reads as "FIGS. 9-13 T" and should read as "FIGS. 9-13"

Signed and Sealed this
Eighth Day of September, 2020

Andrei Iancu
*Director of the United States Patent and Trademark Office*